(12) United States Patent
Liverton et al.

(10) Patent No.: US 8,828,930 B2
(45) Date of Patent: Sep. 9, 2014

(54) HEPATITIS C VIRUS NS3 PROTEASE INHIBITORS

(75) Inventors: Nigel J. Liverton, Harleysville, PA (US); John A. McCauley, Maple Glen, PA (US); Michael T. Rudd, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 194 days.

(21) Appl. No.: 13/387,542

(22) PCT Filed: Jul. 27, 2010

(86) PCT No.: PCT/US2010/043340
§ 371 (c)(1),
(2), (4) Date: Jan. 27, 2012

(87) PCT Pub. No.: WO2011/014487
PCT Pub. Date: Feb. 3, 2011

(65) Prior Publication Data
US 2012/0121624 A1     May 17, 2012

Related U.S. Application Data

(60) Provisional application No. 61/229,790, filed on Jul. 30, 2009.

(51) Int. Cl.
*A61K 38/00* (2006.01)
*A01N 37/18* (2006.01)

(52) U.S. Cl.
USPC .................................................. 514/3.7

(58) Field of Classification Search
None
See application file for complete search history.

(56) References Cited

U.S. PATENT DOCUMENTS

| | | |
|---|---|---|
| 3,480,613 A | 11/1969 | Walton |
| 6,323,180 B1 | 11/2001 | Llinas-Brunet et al. |
| 6,608,027 B1 | 8/2003 | Tsantrizos et al. |
| 6,777,395 B2 | 8/2004 | Bhat et al. |
| 6,995,174 B2 | 2/2006 | Wang et al. |
| 6,995,177 B1 | 2/2006 | Bianchi et al. |
| 7,091,209 B2 | 8/2006 | Gardelli et al. |
| 7,119,073 B2 | 10/2006 | Colarusso et al. |
| 7,470,664 B2 | 12/2008 | Holloway et al. |
| 7,662,809 B2 | 2/2010 | Ercolani et al. |
| 7,767,660 B2 | 8/2010 | Stansfield et al. |
| 7,781,422 B2 | 8/2010 | Stansfield et al. |
| 7,781,431 B2 | 8/2010 | Attenni et al. |
| 7,795,247 B2 | 9/2010 | Conte et al. |
| 7,795,250 B2 | 9/2010 | Colarusso et al. |
| 7,879,797 B2 | 2/2011 | Holloway et al. |
| 7,973,026 B2 | 7/2011 | Colarusso et al. |
| 7,973,040 B2 | 7/2011 | Harper et al. |
| 7,989,438 B2 | 8/2011 | Conte et al. |
| 8,012,982 B2 | 9/2011 | Conte et al. |
| 8,080,654 B2 | 12/2011 | Harper et al. |
| 8,101,595 B2 | 1/2012 | Stansfield et al. |
| 8,138,164 B2 | 3/2012 | Liverton et al. |
| 8,178,333 B2 | 5/2012 | Mijts et al. |
| 8,178,520 B2 | 5/2012 | Di Francesco et al. |
| 8,183,216 B2 | 5/2012 | Di Francesco et al. |
| 8,216,999 B2 | 7/2012 | Holloway et al. |
| 8,232,390 B2 | 7/2012 | Capito et al. |
| 8,278,322 B2 | 10/2012 | Holloway et al. |
| 8,309,540 B2 | 11/2012 | Liverton et al. |
| 8,314,062 B2 | 11/2012 | Crescenzi et al. |
| 8,377,873 B2 | 2/2013 | Liverton et al. |
| 8,377,874 B2 | 2/2013 | Liverton et al. |
| 2002/0019363 A1 | 2/2002 | Ismaili et al. |
| 2002/0107138 A1 | 8/2002 | Hoveyda et al. |
| 2003/0236216 A1 | 12/2003 | Devos et al. |
| 2004/0006007 A1 | 1/2004 | Gosselin et al. |
| 2004/0063658 A1 | 4/2004 | Roberts et al. |
| 2004/0067901 A1 | 4/2004 | Bhat et al. |
| 2004/0106627 A1 | 6/2004 | Gardelli et al. |
| 2004/0142876 A1 | 7/2004 | Colarusso et al. |
| 2004/0229776 A1 | 11/2004 | Chen et al. |

(Continued)

FOREIGN PATENT DOCUMENTS

| | | |
|---|---|---|
| EP | 1719773 A1 | 11/2006 |
| GB | 2337262 A | 11/1999 |

(Continued)

OTHER PUBLICATIONS

Aeberli, Paul et al., "Neuropharmacological investigation of N-benzylsulfamides," 10(4) J. Med. Chem. 636-42 (1967).

(Continued)

*Primary Examiner* — Thomas Heard
(74) *Attorney, Agent, or Firm* — Sheldon O. Heber; Julie M. Lake

(57) ABSTRACT

The present invention relates to macrocyclic compounds of Formula (I) that are useful as inhibitors of the hepatitis C virus (HCV) NS3 protease, their synthesis, and their use for treating or preventing HCV infections.

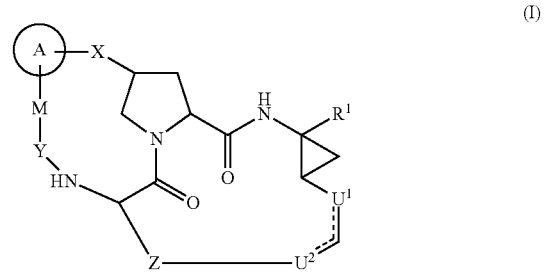

6 Claims, No Drawings

(56) References Cited

U.S. PATENT DOCUMENTS

| | | |
|---|---|---|
| 2004/0229818 A1 | 11/2004 | Llinas-Brunet |
| 2004/0254159 A1 | 12/2004 | Hasvold et al. |
| 2004/0266668 A1 | 12/2004 | Nakajima et al. |
| 2005/0020503 A1 | 1/2005 | Llinas-Brunet et al. |
| 2005/0038240 A1 | 2/2005 | Connolly et al. |
| 2005/0130997 A1 | 6/2005 | Avolio et al. |
| 2006/0100262 A1 | 5/2006 | Conte et al. |
| 2006/0257980 A1 | 11/2006 | Li |
| 2007/0027071 A1 | 2/2007 | Holloway et al. |
| 2007/0072911 A1 | 3/2007 | Avolio et al. |
| 2007/0167447 A1 | 7/2007 | Avolio et al. |
| 2007/0259959 A1 | 11/2007 | Cortese et al. |
| 2008/0139596 A1 | 6/2008 | De Francesco et al. |
| 2008/0153895 A1 | 6/2008 | Stansfield et al. |
| 2008/0200513 A1 | 8/2008 | Colarusso et al. |
| 2008/0214522 A1 | 9/2008 | Stansfield et al. |
| 2008/0249146 A1 | 10/2008 | Conte et al. |
| 2008/0261938 A1 | 10/2008 | Ercolani et al. |
| 2008/0261944 A1 | 10/2008 | Colarusso et al. |
| 2009/0036443 A1 | 2/2009 | Attenni et al. |
| 2009/0048239 A1 | 2/2009 | Conte et al. |
| 2009/0069344 A1 | 3/2009 | Conte et al. |
| 2009/0075869 A1 | 3/2009 | Holloway et al. |
| 2009/0105227 A1 | 4/2009 | Colarusso et al. |
| 2009/0124661 A1 | 5/2009 | Holloway et al. |
| 2009/0203008 A1 | 8/2009 | Ludmerer et al. |
| 2009/0258891 A1 | 10/2009 | Di Francesco et al. |
| 2009/0312241 A1 | 12/2009 | Crescenzi et al. |
| 2010/0009959 A1 | 1/2010 | Capito et al. |
| 2010/0029666 A1 | 2/2010 | Harper et al. |
| 2010/0076046 A1 | 3/2010 | Stansfield et al. |
| 2010/0093779 A1 | 4/2010 | Liverton et al. |
| 2010/0099695 A1 | 4/2010 | Liverton et al. |
| 2010/0120760 A1 | 5/2010 | Koch et al. |
| 2010/0152128 A1 | 6/2010 | Attenni et al. |
| 2010/0183551 A1 | 7/2010 | Harper et al. |
| 2010/0210581 A1 | 8/2010 | Di Francesco et al. |
| 2010/0286185 A1 | 11/2010 | Liverton et al. |
| 2010/0298210 A1 | 11/2010 | Liverton et al. |
| 2010/0317623 A1 | 12/2010 | Liverton et al. |
| 2011/0002884 A1 | 1/2011 | McCauley et al. |
| 2011/0028494 A1 | 2/2011 | Holloway et al. |
| 2011/0046161 A1 | 2/2011 | Liverton et al. |
| 2011/0224134 A1 | 9/2011 | Harper et al. |
| 2012/0121624 A1 | 5/2012 | Liverton et al. |
| 2012/0232247 A1 | 9/2012 | Song et al. |
| 2012/0289709 A1 | 11/2012 | Lalonde et al. |

FOREIGN PATENT DOCUMENTS

| | | | |
|---|---|---|---|
| GB | 2430621 A | | 4/2007 |
| WO | 9741211 A1 | | 11/1997 |
| WO | 9822496 A2 | | 5/1998 |
| WO | 9846630 A1 | | 10/1998 |
| WO | 9907733 A2 | | 2/1999 |
| WO | 9907734 A2 | | 2/1999 |
| WO | 9938888 A1 | | 8/1999 |
| WO | 9943691 A1 | | 9/1999 |
| WO | 9950230 A1 | | 10/1999 |
| WO | 9964442 A1 | | 12/1999 |
| WO | 0009543 A2 | | 2/2000 |
| WO | 0009546 A2 | | 2/2000 |
| WO | 0025780 A1 | | 5/2000 |
| WO | 0059929 A1 | | 10/2000 |
| WO | 0100622 A1 | | 1/2001 |
| WO | 0147883 A1 | | 7/2001 |
| WO | 0160379 A1 | | 8/2001 |
| WO | 0168663 A1 | | 9/2001 |
| WO | 0177091 A2 | | 10/2001 |
| WO | 0177113 A2 | | 10/2001 |
| WO | 0179246 A2 | | 10/2001 |
| WO | 0190121 A2 | | 11/2001 |
| WO | 0192282 A2 | | 12/2001 |
| WO | 0204425 A1 | | 1/2002 |
| WO | 0206246 A1 | | 1/2002 |
| WO | 0218404 A1 | | 3/2002 |
| WO | 0220497 A1 | | 3/2002 |
| WO | 0232920 A2 | | 4/2002 |
| WO | 0232930 A2 | | 4/2002 |
| WO | 0248116 A2 | | 6/2002 |
| WO | 0248165 A2 | | 6/2002 |
| WO | 0248172 A2 | | 6/2002 |
| WO | 02051425 A1 | | 7/2002 |
| WO | 02057287 A2 | | 7/2002 |
| WO | 02057425 A2 | | 7/2002 |
| WO | 02100415 A2 | | 12/2002 |
| WO | 03015755 A2 | | 2/2003 |
| WO | 03026589 A2 | | 4/2003 |
| WO | 03026675 A1 | | 4/2003 |
| WO | 03062192 A1 | | 7/2003 |
| WO | 03062211 A1 | | 7/2003 |
| WO | 03064455 A2 | | 8/2003 |
| WO | 03068244 A1 | | 8/2003 |
| WO | 03093290 A2 | | 11/2003 |
| WO | 03099274 A1 | | 12/2003 |
| WO | 2004000858 A2 | | 12/2003 |
| WO | 2004002422 A2 | | 1/2004 |
| WO | 2004002999 A2 | | 1/2004 |
| WO | 2004003000 A2 | | 1/2004 |
| WO | 2004003138 A2 | | 1/2004 |
| WO | 2004007512 A2 | | 1/2004 |
| WO | 2004011478 A2 | | 2/2004 |
| WO | 2004013300 A2 | | 2/2004 |
| WO | 2004028481 A2 | | 4/2004 |
| WO | 2004041201 A2 | | 5/2004 |
| WO | 2004087714 A1 | | 10/2004 |
| WO | 2004093915 A1 | | 11/2004 |
| WO | 2004103996 A1 | | 12/2004 |
| WO | 2004110442 A1 | | 12/2004 |
| WO | 2005003147 A2 | | 1/2005 |
| WO | 2005016927 A1 | | 2/2005 |
| WO | 2005023819 A1 | | 3/2005 |
| WO | 2005034941 A1 | | 4/2005 |
| WO | 2005046712 A1 | | 5/2005 |
| WO | 2005070955 A1 | | 8/2005 |
| WO | 2005080399 A1 | | 9/2005 |
| WO | 2006008556 A1 | | 1/2006 |
| WO | 2006020082 A1 | | 2/2006 |
| WO | 2006021341 A1 | | 3/2006 |
| WO | 2006027628 A2 | | 3/2006 |
| WO | 2006029912 A1 | | 3/2006 |
| WO | 2006046030 A1 | | 5/2006 |
| WO | 2006046039 A2 | | 5/2006 |
| WO | 2006102087 A2 | | 9/2006 |
| WO | 2006119061 A2 | | 11/2006 |
| WO | 2006119975 A1 | | 11/2006 |
| WO | 2007015787 A1 | | 2/2007 |
| WO | 2007015855 A1 | | 2/2007 |
| WO | 2007016441 A1 | | 2/2007 |
| WO | 2007028789 A1 | | 3/2007 |
| WO | 2007029029 A2 | | 3/2007 |
| WO | 2007131966 A1 | | 11/2007 |
| WO | 2007145894 A2 | | 12/2007 |
| WO | 2007148135 A1 | | 12/2007 |
| WO | 2008051475 A2 | | 5/2008 |
| WO | 2008051477 A2 | | 5/2008 |
| WO | 2008051514 A2 | | 5/2008 |
| WO | 2008057208 A2 | | 5/2008 |
| WO | 2008057209 A1 | | 5/2008 |
| WO | 2008112108 A1 | | 9/2008 |
| WO | 2009005687 A1 | | 1/2009 |
| WO | 2009010804 A1 | | 1/2009 |
| WO | 2009064955 A1 | | 5/2009 |
| WO | 2009064975 A1 | | 5/2009 |
| WO | 2009108507 A1 | | 9/2009 |
| WO | 2009134624 A1 | | 11/2009 |
| WO | 2010011566 A1 | | 1/2010 |
| WO | 2011014487 A1 | | 2/2011 |
| WO | 2011025849 A1 | | 3/2011 |
| WO | 2012040040 A1 | | 3/2012 |
| WO | 2012078482 A1 | | 6/2012 |
| WO | 2012082672 A1 | | 6/2012 |
| WO | 2012151271 A1 | | 11/2012 |

(56) References Cited

FOREIGN PATENT DOCUMENTS

| WO | 2012151283 A1 | 11/2012 |
|---|---|---|
| WO | 2013028465 A1 | 2/2013 |
| WO | 2013028470 A1 | 2/2013 |
| WO | 2013028471 A1 | 2/2013 |

OTHER PUBLICATIONS

Ahmad, Yusuf et al., Quinoxaline Derivatives. XI. The Reaction of Quinoxaline 1,4-Dioxide and Some of Its Derivatives with Acetyl Chloride, 38(12) J. Org. Chem. 2176 (1973).

Allison, Anthony C. & Elsie M. Eugui, "Immunosuppressive and other anti-rheumatic activities of mycophenolate mofetil," 44 Agents and Actions Supplements 165-88 (1993).

Arasappan, Ashok et al., "P2-P4 Macrocyclic inhibitors of hepatitis C virus NS3-4A serine protease," 16 Bioorganic & Medicinal Chemistry Letters 3960-65 (2006).

Bartenschlager, Ralf, "Candidate Targets for Hepatitis C Virus-Specific Antiviral Therapy," 40(5-6) Intervirology 378-93 (1997).

Beaulieu, Pierre J. et al., Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease, 70 J. Org. Chem. 5869 (2005).

Becker, D. & N. Haddad, "Steric Effects in Intramolecular [2+2] Photocycloaddition of C=C Double Bonds to Cyclohexenones," 49(4) Tetrahedron 947-64 (1993).

Balsano, C., Recent Advances in Antiviral Agents: Established and Innovative Therapies for Viral Hepatitis, 8(4) Mini-Rev. Med. Chem. 307 (2008).

Bunce, Richard A. et al., "Tandem SN2-Michael Reactions for the Preparation of Simple Five- and Six-Membered-Ring Nitrogen and Sulfur Heterocycles," 57 J. Org. Chem. 1727-33 (1992).

Carroll, Steven S. et al., Inhibition of Hepatitis C Virus RNA Replication by 2'-Modified Nucleoside Analogs, 278 (14) J. Biological Chemistry 11979 (2003).

Casini, Angela et al., "Carbonic Anhydrase inhibitors inhibition of cytosolic isozymes I and II with sulfamide derivatives," 13(5) Bioorg. Med. Chem. Lett. 837-40 (2003).

Chakaborty, T. K. et al., "Alpha-Phenylglycinol as chiral auxilliary in diastereoselective Strecker synthesis of alpha-amino acids," 51(33) Tetrahedron 9179-90 (1995).

Chen, Kevin X. et al. "Novel Potent Hepatitis C Virus NS3 Serine Protease Inhibitors Derived from Proline-Based Macrocycles," 49 J. Med. Chem. 995-1005 (2006).

Coates, Robert M. & Mark W. Johnson, "Stereoselective Synthesis of Moenocinol and Assignment of Its Carbon-13 Nuclear Magnetic Resonance Spectrum," 45 J. Org. Chem. 2685-97 (1980).

Conti, Paola et al., "Chemoenzymatic Synthesis of the Enantiomers of Desoxymuscarine," 9 Tetrahedron: Asymmetry 657-65 (1998).

Cooke, Michael D. et al., "The occurrence of a hydride shift in the aromatization of 1,4-epoxy-1,2-dihydronaphthalenes," 11 J. Chem. Soc. Perkin Trans. I: Phys. Org. Chem. 1377 (1984).

Crabb, Charlene, Infectious Diseases. "Hard-Won Advances Spark Excitement about Hepatitis C," Science 506-507 (2001).

De Francesco, Raffaele et al., Approaching a new era for hepatitis C virus therapy: inhibitors of the NS3-4A serine protease and the NS5B RNA-dependent RNA polymerase, 58 Antiviral Research 1 (2003).

Dymock, Brain W., "Emerging therapies for hepatitis C virus infection," 6 Emerging Drugs 13-42 (2001).

Dymock, Brian W. et al., "Novel Approaches to the Treatment of Hepatitis C Virus Infection," 11 Antiviral Chemistry & Chemotherapy 79-96 (2000).

Eicher, Theophil et al., "Bryophyte Constituents; 7: New Synthesis of (+)-Rosmarinic Acid and Related Compounds," Synthesis 755-62 (Jun. 1996).

Fürstner, Alois et al., Total Synthesis and Structural Refinement of the Cyclic Tripyrrole Pigment Nonylprodigiosin, 64 J. Org. Chem. 8275 (1999).

Gallinari, Paola et al., Modulation of Hepatitis C Virus NS3 Protease and Helicase Activities through the Interaction with NS4A, 38 Biochem. 5620 (1999).

Gallinari, Paola et al., Multiple Enzymatic Activities Associated with Recombinant NS3 Protein of Hepatitis C Virus, 72(8) J. Virology 6758 (1998).

Goldberg, Yuri et al., "Highly regioselective bromination of 2,3-dimethylanisole with N-bromosuccinimide," 57 J. Org. Chem. 6374-76 (1992).

Goudreau, Nathalie & Montse Llinas-Brunet, "The Therapeutic Potential of NS3 Protease Inhibitors in HCV Infection," 14(9) Expert Opinion 1129-44 (2005).

Haner, Robert et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Harry-O'Kuru, Rogers E. et al., A Short, Flexible Route toward 2'-C-Branched Ribonucleosides, 62 J. Org. Chem. 1754 (1997).

Hon, Yung-Son et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

House, Herbert O. et al., "Cyclization of Unsaturated Hydroxylamine Derivatives," 41(5) J. Org. Chem. 855-63 (1976).

International Preliminary Report on Patentability, International Application No. PCT/US2011/051871, dated Mar. 26, 2013.

Juaristi, Eusebio & Hugo A. Jimenez-Vazquez, "Single Electron Transfer Mechanism in the Reaction of 1,3-Dithianyllithium and Alkyl Iodides," 56 J. Org. Chem. 1623-30 (1991).

Kingsbury, Jason S. et al., A Recyclable Ru-Based Metathesis Catalyst, 121 J. Am. Chem. Soc. 791 (1999).

Kirschbaum, Joel, "Amantadine," 12 Profiles of Drug Substances, Excipients and Related Methodology 1-36 (1983).

Lauer, Georg M. & Bruce D. Walker, "Hepatitis C Virus Infection," 345(1) N. Engl. J. Med. 41-52 (2001); correction: 345(19) N. Engl. J. Med. 1425-26 (2001).

Liverton, Nigel J. et al., Molecular Modeling Based Approach to Potent P2-P4 Macrocyclic Inhibitors of Hepatitis C NS3/NS4A Protease, 130 J. Am. Chem. Soc. 4607-09 (2008).

Lohmann, V. et al., "Replication of Subgenomic Hepatitis C Virus RNAs in a Hepatoma Cell Line," 285 Science 110-13 (1999).

Lohmann, Volker et al., "Selective Stimulation of Hepatitis C Virus and Pestivirus NS5B RNA Polymerase Activity by GTP," 274(16) J. Bio. Chem. 10807-15 (1999).

Ludmerer, Steven W. et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

Mao, Shi-Shan et al., A time-resolved, internally quenched fluorescence assay to characterize inhibition of hepatitis C virus nonstructural protein 3-4A protease at low enzyme concentrations, 373 Analytical Biochemistry 1 (2008).

McCauley, John A. et al., "Bismacrocyclic Inhibitors of Hepatitis C NS3/4a Protease," 47 Angew. Chem. Int. Ed. 9104-07 (2008).

Miller, Scott J. et al., Application of Ring-Closing Metathesis to the Synthesis of Rigidified Amino Acids and Peptides, 118 J. Am. Chem. Soc. 9606 (1996).

Mitsunobu, Oyo, The Use of Diethyl Azodicarboxylate and Triphenylphosphine in Synthesis and Transformation of Natural Products, Synthesis 1 (Jan. 1981).

Moradpour, Darius & Hubert E. Blum, "Current and evolving therapies for hepatitis C," 11 Euro. J. Gastroenterol. Hepatol. 1189-1202 (1999).

Onisuka, Kiyotaka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Poupart, Marc-Andre et al., "Solid-Phase Synthesis of Peptidomimetic Inhibitors for the Hepatitis C Virus NS3 Protease," 66(14) J. Org. Chem. 4743-51 (2001).

(56) References Cited

OTHER PUBLICATIONS

Rönn, Robert & Sandstrom, Anja, New Developments in the Discovery of Agents to Treat Hepatitis C, 8 Current Topics Med. Chem. 533 (2008).

Rosen, Hugo R. & David R. Gretch, "Hepatitis C virus: current understanding and prospects for future therapies," 5 Molec. Med. Today 393-99 (1999).

Rudisill, Duane E. & J. K. Stille, "Palladium-catalyzed synthesis of 2-substituted indoles," 54(25) J. Org. Chem. 5856-66 (2002).

Satoh, Makoto et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Schlosser, Manfred et al., "8-Methoxyisoquinoline derivatives through ortho-selective metallation of 2-(3-methoxyphenyl)ethylamines," 32(17) Tetrahedron Letters 1965-66 (1991).

Scholl, Matthias et al., Synthesis and Activity of a New Generation of Ruthenium-Based Olefin Metathesis Catalysts Coordinated with 1,3-Dimesityl-4,5-dihydroimidazol-2-ylidene Ligands, 1(6) Organic Letters 953 (1999).

Sheldon, Julie et al., Novel protease and polymerase inhibitors for the treatment of hepatitis C virus infection, 16(8) Expert Opin. Investig. Drugs 1171 (2007).

Srikrishna, A. et al., "Enantiospecific Construction of the BC-ring System of Taxanes," 45 Tetrahedron Letters 2939-42 (2004).

Still, W. Clark et al., "Rapid Chromatographic Technique for Preparative Separations with Moderate Resolution," 43 (14) J. Org. Chem. 2923-25 (1978).

Taliani, Mariana et al., A Continuous Assay of Hepatitis C Virus Protease Based on Resonance Energy Transfer Depsipeptide Substrates, 240 Anal. Biochem. 60 (1996).

Tokuda, Masao et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Trnka, Tina M. & Robert H. Grubbs, The Development of $L_2X_2Ru$=CHR Olefin Metathesis Catalysts: An Organometallic Success Story, 34 Acc. Chem. Res. 18 (2001).

Tsantrizos, Youla S., The Design of a Potent Inhibitor of the Hepatitis C Virus NS3 Protease: BILN 2061—From the NMR Tube to the Clinic, Biopolymers (Peptide Science), vol. 76, pp. 309-323 (2004).

Venuti, Michael C. et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Vrolijk, Jan M. et al., A replicon-based bioassay for the measurement of interferons in patients with chronic hepatitis C, 110 J. Virological Methods 201 (2003).

Wolfe, Michael S. & Rogers E. Harry-O'Kuru, "A Concise Synthesis of 2'-C-Methylribonucleosides," 36(42) Tetrahedron Letters 7611-14 (1995).

Yan, Youwei et al., Complex of NS3 protease and NS4A peptide of BK strain hepatitis C virus: A 2.2 Angstrom resolution structure in a hexagonal crystal form, 7 Protein Science 837 (1998).

Yokoyama, Yuusaku et al., "Palladium-Catalyzed Reaction of 3-Bromoindole Derivative with Allyl Esters in the Presence of Hexa-n-butyldistannane," 31(8) Heterocycles 1505-11 (1990).

HEPATITIS C VIRUS NS3 PROTEASE INHIBITORS

CROSS-REFERENCE TO RELATED APPLICATIONS

This application is a National Stage application of International Patent Application No. PCT/US10/43340, filed Jul. 27, 2010, which claims priority to Provisional Patent Application No. 61/229,790, filed Jul. 30, 2009.

FIELD OF THE INVENTION

The present invention relates to macrocyclic compounds that are useful as inhibitors of the hepatitis C virus (HCV) NS3 (non-structural 3) protease, their synthesis, and their use for treating or preventing HCV infection.

BACKGROUND OF THE INVENTION

Hepatitis C viral infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

Potential treatments for HCV infection has been discussed in the different references including C. Blasano, *Recent Advances in Antiviral Agents: Established and Innovative Therapies for Viral Hepatitis*, 8(4) MINI-REV. MED. CHEM. 307 (2008); Robert Rönn & Anja Sandstrom, *New Developments in the Discovery of Agents to Treat Hepatitis C*, 8 CURRENT TOPICS MED. CHEM. 533 (2008); Julie Sheldon et al., *Novel protease and polymerase inhibitors for the treatment of hepatitis C virus infection*, 16(8) EXPERT OPIN. INVESTIG. DRUGS 1171 (2007); and Raffaele De Francesco et al., *Approaching a new era for hepatitis C virus therapy: inhibitors of the NS3-4A serine protease and the NS5B RNA-dependent RNA polymerase*, 58 ANTIVIRAL RESEARCH 1 (2003).

There is a clear and long-felt need to develop effective therapeutics for treatment of HCV infection. Specifically, there is a need to develop compounds that are useful for treating HCV-infected patients and compounds that selectively inhibit HCV viral replication. Thus, there is a need for compounds that are effective inhibitors of the NS3 protease.

SUMMARY OF THE INVENTION

The present invention relates to novel macrocyclic compounds of Formula I and/or pharmaceutically acceptable salts or hydrates thereof. These compounds are useful in the inhibition of HCV NS3 protease, the prevention or treatment of one or more of the symptoms of HCV infection, either as compounds or their pharmaceutically acceptable salts or hydrates (when appropriate), or as pharmaceutical composition ingredients, whether or not in combination with other HCV antivirals, anti-infectives, immunomodulators, antibiotics or vaccines.

More particularly, the present invention relates to a compound of Formula I:

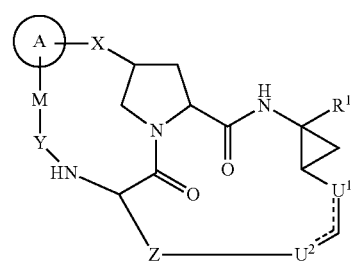

and/or a pharmaceutically acceptable salt, hydrate or prodrug thereof, wherein:

is selected from the group of rings consisting of:
1) an aryl,
2) a $C_3$-$C_8$ cycloalkyl; and
3) a heterocyclic ring system selected from the group consisting of:
   a) a 5- or 6-membered saturated or unsaturated monocyclic ring with 1, 2, or 3 heteroatom ring atoms each independently selected from the group consisting of N, O or S,
   b) a 8-, 9- or 10-membered saturated or unsaturated bicyclic ring with 1, 2, or 3 heteroatom ring atoms each independently selected from the group consisting of N, O or S, and
   c) a 11- to 15-membered saturated or unsaturated tricyclic ring with 1, 2, 3, or 4 heteroatom ring atoms each independently selected from the group consisting of N, O or S, wherein:
   i) the aryl or cycloalkyl ring has from 0 to 4 independently substituents $R^2$,
   ii) the heterocyclic ring has from 0 to 4 independently selected $R^2$ substitutions, and
   iii) points of attachment to variables M and X are independently selected from a first pair of atoms comprising a first carbon ring atom and second carbon ring atom, and a second pair of atoms comprising a carbon ring atom and a nitrogen ring atom;

$R^1$ is selected from the group consisting of $CO_2R^3$, $CONR^3SO_2R^4$, $CONR^3SO_2NR^5R^6$, tetrazolyl, $CONHP(O)R^7R^8$, and $P(O)R^7R^8$;

$R^2$ selected from the group consisting of H, halo, $OR^3$, $C(O)R^3$, $CO_2R^3$, $C_1$-$C_6$ alkyl, CN, $CF_3$, $SR^3$, $SO_2(C_1$-$C_6$ alkyl), $C_3$-$C_8$ cycloalkyl, $C_3$-$C_8$ cycloalkoxy, $C_1$-$C_6$ haloalkyl, $N(R^9)_2$, oxo, phenyl, naphthyl, Het A and Het B,
   wherein the $R^2$ phenyl, naphthyl, Het A, Het B, cycloalkyl, cycloalkoxy, alkyl or alkoxy is substituted with from 0 to 4 substituents selected from the group consisting of halo, $OR^3$, $SR^3$, $N(R^9)_2$, $N(C_1$-$C_6$ alkyl)($C_1$-$C_6$ alkoxy), $C_1$-$C_6$ alkyl, $C_1$-$C_6$ haloalkyl, $C_1$-$C_6$ haloalkoxy, $C_3$-$C_6$ cycloalkyl, $C_3$-$C_6$ cycloalkoxy, $NO_2$, CN, $CF_3$, $SO_2(C_1$-$C_6$ alkyl), $NR^3SO_2R^4$, $SO_2N(R^4)_2$, $S(O)(C_1$-$C_6$ alkyl), $NHC(O)OR^4$, $NHC(O)R^4$, $NHC(O)NHR^4$, $CO_2R^3$, $C(O)R^3$, and $C(O)N(R^3)_2$, wherein 2 adjacent substituents of the $R^2$ cycloalkyl, cycloalkoxy, phenyl, naphthyl, Het A or Het B are optionally taken together to form a 3- to 6-membered cyclic ring containing from 0 to 3 heteroatoms selected from N, O and S, and wherein any $R^2$ oxo substituent, if present, is located on a carbon or sulfur ring atom;

Het A is a 5- or 6-membered aromatic ring having 1, 2 or 3 heteroatoms selected from N, O and S, attached through a ring carbon or nitrogen;

Het B is a 5- to 7-membered saturated or unsaturated non-aromatic ring having 1, 2, 3 or 4 heteroatoms selected from N, O and S, attached through a ring carbon or nitrogen;

each $R^3$ is independently selected from the group consisting of H, $C_1$-$C_6$ alkyl, phenyl and naphthyl;

each $R^4$ is independently selected from the group consisting of $C_1$-$C_6$ alkyl, $C_3$-$C_6$ cycloalkyl, $C_3$-$C_6$ cycloalkyl($C_1$-$C_5$ alkyl), phenyl, naphthyl, phenyl($C_1$-$C_4$ alkyl), naphthyl($C_1$-$C_4$ alkyl), Het A, Het A($C_1$-$C_4$ alkyl), Het B, and Het B($C_1$-$C_8$ alkyl), wherein the $R^4$ alkyl, cycloalkyl, phenyl, naphthyl, Het A and Het B is substituted with from 0 to 2 W substituents;

each $R^5$ is independently selected from the group consisting of $C_1$-$C_8$ alkyl, $C_3$-$C_8$ cycloalkyl, $C_3$-$C_8$ cycloalkyl($C_1$-$C_8$ alkyl), phenyl, naphthyl, phenyl($C_1$-$C_4$ alkyl), naphthyl($C_1$-$C_4$ alkyl), Het A, Het A($C_1$-$C_4$ alkyl), Het B, and Het B($C_1$-$C_8$ alkyl), wherein the $R^5$ alkyl, cycloalkyl, phenyl, naphthyl, phenyl($C_1$-$C_4$ alkyl), naphthyl($C_1$-$C_4$ alkyl), Het A, or Het B is substituted with from 0 to 4 substituents selected from the group consisting of phenyl, naphthyl, $C_3$-$C_8$ cycloalkyl, Het A, Het B, $C_1$-$C_6$ alkyl, $C_1$-$C_6$ haloalkoxy, halo, $OR^3$, $SR^3$, $N(R^3)_2$, $N(C_1$-$C_6$ alkyl)($C_1$-$C_6$ alkoxy), $C_1$-$C_6$ alkyl, $C(O)R^3$, $C_1$-$C_6$ haloalkyl, $NO_2$, CN, $CF_3$, $SO_2(C_1$-$C_6$ alkyl), $S(O)(C_1$-$C_6$ alkyl), $NR^3SO_2R^4$, $SO_2N(R^4)_2$, $NHC(O)OR^4$, $NHC(O)R^4$, $NHC(O)NHR^4$, $CO_2R^3$, and $C(O)N(R^3)_2$, and wherein 2 adjacent substituents of the $R^5$ cycloalkyl, cycloalkoxy, aryl, heteroaryl or heterocyclyl are optionally taken together to form a 3- to 6-membered cyclic ring containing from 0 to 3 heteroatoms selected from N, O and S;

each $R^6$ is independently selected from the group consisting of $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, phenyl, naphthyl, phenyl($C_1$-$C_4$ alkyl), naphthyl($C_1$-$C_4$ alkyl), Het A, Het A($C_1$-$C_4$ alkyl), Het B, and Het B($C_1$-$C_8$ alkyl), wherein the $R^6$ alkyl, cycloalkyl, alkoxy, cycloalkoxy, phenyl, naphthyl, Het A and Het B is substituted with from 0 to 4 substituents selected from the group consisting of phenyl, naphthyl, Het A, Het B, $C_3$-$C_8$ cycloalkyl, $C_1$-$C_6$ alkyl, $C_1$-$C_6$ haloalkoxy, halo, $OR^3$, $SR^3$, $N(R^3)_2$, $N(C_1$-$C_6$ alkyl)($C_1$-$C_6$ alkoxy), $C_1$-$C_6$ alkyl, $C(O)R^3$, $C_1$-$C_6$ haloalkyl, $NO_2$, CN, $CF_3$, $SO_2(C_1$-$C_6$ alkyl), $S(O)(C_1$-$C_6$ alkyl), $NR^3SO_2R^4$, $SO_2N(R^4)_2$, $NHC(O)OR^4$, $NHC(O)R^4$, $NHC(O)NHR^4$, $CO_2R^3$, and $C(O)N(R^3)_2$; and wherein 2 adjacent substituents of the $R^6$ cycloalkyl, cycloalkoxy, aryl, heteroaryl or heterocyclyl are optionally taken together to form a 3- to 6-membered cyclic ring containing from 0 to 3 heteroatoms selected from N, O and S;

or $R^5$ and $R^6$ are optionally taken together, with the nitrogen atom to which they are attached, to form a 4- to 8-membered monocyclic ring containing from 0 to 2 additional heteroatoms selected from N, O and S;

each $R^7$ is independently selected from the group consisting of $OR^{14}$, $N(R^3)$—V—$CO_2R^3$, O—V—$CO_2R^3$, S—V—$CO_2R^3)N(R^3)(R^{10})$, $R^{11}$, and $N(R^3)SO_2R^4$;

each $R^8$ is independently selected from the group consisting of $OR^{14}$, $N(R^3)$—V—$CO_2R^3$, O—V—$CO_2R^3$, S—V—$CO_2R^3$, and $N(R^3)(R^{10})$;

or $R^7$ and $R^8$ are optionally taken together, with the phosphorus atom to which they are attached, to form a 5- to 7-membered monocyclic ring;

each $R^9$ is independently selected from the group consisting of H, $C_1$-$C_6$ alkyl, $C_3$-$C_6$ cycloalkyl, $C_3$-$C_6$ cycloalkyl($C_1$-$C_5$ alkyl), phenyl, naphthyl, phenyl($C_1$-$C_4$ alkyl), naphthyl($C_1$-$C_4$ alkyl), Het A, Het A($C_1$-$C_4$ alkyl), Het B, and Het B($C_1$-$C_8$ alkyl), wherein the $R^9$ alkyl, cycloalkyl, phenyl, naphthyl, Het A or Het B is substituted with from 0 to 2 W substituents;

each V is independently selected from the group consisting of —$CH(R^{12})$— and —$C_1$-$C_4$ alkylene-$CH(R^{12})$—;

each $R^{10}$ is independently selected from the group consisting of H, $C_1$-$C_6$ alkyl, $C_2$-$C_6$ alkenyl, $C_3$-$C_8$ cycloalkyl, phenyl, naphthyl, Het A and Het B, wherein the $R^{10}$ alkyl, alkenyl, cycloalkyl, phenyl, naphthyl, Het A or Het B is substituted with from 0 to 2 substituents selected from the group consisting of phenyl, naphthyl, phenyl($C_1$-$C_4$ alkyl), naphthyl($C_1$-$C_4$ alkyl), Het A, Het A($C_1$-$C_4$ alkyl), Het B, Het B($C_1$-$C_8$ alkyl), $C_1$-$C_6$ alkyl, halo, $OC(O)OR^4$, $OC(O)R^4$, $OR^3$, $SR^3$, $N(R^3)_2$, $C(O)R^3$, $NO_2$, CN, $CF_3$, $SO_2(C_1$-$C_6$ alkyl), $S(O)(C_1$-$C_6$ alkyl), $NR^3SO_2R^4$, $SO_2N(R^4)_2$, $NHC(O)OR^4$, $NHC(O)R^4$, $NHC(O)NHR^4$, $CO_2R^3$, and $C(O)N(R^3)_2$; and wherein 2 adjacent substituents of the $R^{10}$ cycloalkyl, cycloalkoxy, phenyl, naphthyl, Het A or Het B are optionally taken together to form a 3- to 6-membered cyclic ring containing from 0 to 3 heteroatoms selected from N, O and S;

each $R^{11}$ is independently selected from the group consisting of $C_1$-$C_6$ alkyl, $C_2$-$C_6$ alkenyl, phenyl, naphthyl, and Het A, wherein the $R^{11}$ phenyl, naphthyl, or Het A is substituted with from 0 to 2 substituents selected from the group consisting of $C_1$-$C_6$ alkyl, halo, $OC(O)OR^4$, $OC(O)R^4$, $OR^3$, $SR^3$, $N(R^3)_2$, $C(O)R^3$, $NO_2$, CN, $CF_3$, $SO_2(C_1$-$C_6$ alkyl), $S(O)(C_1$-$C_6$ alkyl), $NR^3SO_2R^4$, $SO_2N(R^4)_2$, $NHC(O)OR^4$, $NHC(O)R^4$, $NHC(O)NHR^4$, $CO_2R^3$, and $C(O)N(R^3)_2$;

each $R^{12}$ is independently selected from the group consisting of $C_1$-$C_6$ alkyl, $C_2$-$C_6$ alkenyl, $C_3$-$C_8$ cycloalkyl, phenyl, naphthyl, Het A and Het B, wherein the $R^{12}$ alkyl, alkenyl, cycloalkyl, phenyl, naphthyl, Het A or Het B is substituted with from 0 to 2 substituents selected from the group consisting of $C_1$-$C_6$ alkyl, halo, $OC(O)OR^4$, $OC(O)R^4$, $OR^3$, $SR^3$, $N(R^3)_2$, $C(O)^{R3}$, $NO_2$, CN, $CF_3$, $SO_2(C_1$-$C_6$ alkyl), $S(O)(C_1$-$C_6$ alkyl), $NR^3SO_2R^4$, $SO_2N(R^4)_2$, $NHC(O)OR^4$, $NHC(O)R^4$, $NHC(O)NHR^4$, $CO_2R^3$, and $C(O)N(R^3)_2$; and wherein 2 adjacent substituents of the $R^{12}$ cycloalkyl, cycloalkoxy, phenyl, naphthyl, Het A or Het B are optionally taken together to form a 3- to 6-membered cyclic ring containing from 0 to 3 heteroatoms selected from N, O and S;

each W is independently selected from the group consisting of halo, $OR^3$, $C_1$-$C_6$ alkyl, CN, $CF_3$, $NO_2$, $SR^3$, $CO_2R^3$, $CON(R^3)_2$, $C(O)R^3$, $N(R^3)C(O)R^3$, $SO_2(C_1$-$C_6$ alkyl), $S(O)(C_1$-$C_6$ alkyl), $C_3$-$C_5$ cycloalkyl, $C_3$-$C_6$ cycloalkoxy, $C_1$-$C_6$ haloalkyl, $N(R^3)_2$, $N(C_1$-$C_6$ alkyl)O($C_1$-$C_6$ alkyl), halo($C_1$-$C_6$ alkoxy), $NR^3SO_2R^3$, $SO_2N(R^3)_2$, $NHCOOR^3$, $NHCONHR^3$, phenyl, naphthyl, Het A and Het B;

Z is selected from the group consisting of $C_3$-$C_9$ alkylene having from 0 to 3 substituents independently selected from $C_1$-$C_6$ alkyl, where 2 such alkyl substituents are optionally taken together to form a spiro or fused ring containing the substituent atoms and shared atom or atoms;

$U^1{\cdots}U^2$ is $U^1{=}U^2$ or $U^1{-}U^2$, where $U^1$ and $U^2$ are each C;
X is selected from the group consisting of:
1) —$C_{0-5}$ alkylene-$X^1$—,
2) —$C_{2-5}$ alkenylene-$X^1$—, and
3) —$C_{2-5}$ alkynylene-$X^1$—,
  wherein $X^1$ is selected from the group consisting of —O—, —NH—, —$CH_2$—, —C(O)O—, —C(O)$NR^{13}$— or —$NR^{13}$C(O)O—, and wherein alkylene, alkenylene and alkynylene is unsubstituted or substituted with from 0 to 3 $C_1$-$C_6$ alkyl, wherein:
    $R^{13}$ is selected from the group consisting of H and $C_1$-$C_6$ alkyl;
Y is selected from the group consisting of —OC(O)—, —$NR^{14}$C(O)—, —C(O)— and —$NHSO_2$—, wherein $R^{14}$ is $C_{1-6}$ alkyl; and
M is selected from the group consisting of $C_1$-$C_{12}$ alkylenes, $C_2$-$C_{12}$ alkenylenes and $C_2$-$C_{12}$ alkynylenes, wherein:
  M contains 0 or 1 —O— moiety in place of a methylene moiety, and
  M is substituted with from 0 to 4 substituents $R^{15}$, wherein:
    each $R^{15}$ is independently selected from the group consisting of $C_1$-$C_8$ alkyl, =$CH_2$, $C_3$-$C_8$ cycloalkyl($C_1$-$C_8$ alkyl), phenyl($C_1$-$C_8$ alkyl) and naphthyl($C_1$-$C_8$ alkyl), and
    any substituent $R^{15}$ may be taken together with any adjacent substituent $R^{15}$ or any adjacent substituent $R^{14}$ to form a 3- to 6-membered ring containing 0 to 3 heteroatoms independently selected from the group consisting of N, O and S.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts and/or hydrates thereof. These compounds and their pharmaceutically acceptable salts and/or hydrates are HCV protease inhibitors (e.g., HCV NS3 protease inhibitors).

In a first embodiment of the invention, (A)

is selected from the group consisting of:
1) an aryl,
2) a cyclohexyl, and
3) a heterocyclic ring system selected from the group consisting of:
  a) a 5- or 6-membered saturated or unsaturated monocyclic ring containing 1, 2, or 3 nitrogen atoms, and
  b) a 8-, 9- or 10-membered saturated or unsaturated bicyclic ring containing 1 or 2 nitrogen atoms, wherein:
1) the aryl or cyclohexyl has from 0 to 4 independently selected substituents $R^2$, and
2) the heterocyclic ring has from 0 to 4 independently selected $R^2$ substitutions. In this embodiment and all aspects of this embodiment described below, all other groups are as provided in the general formula above.

In a first aspect of the first embodiment, (A)

is selected from the group consisting of:

-continued
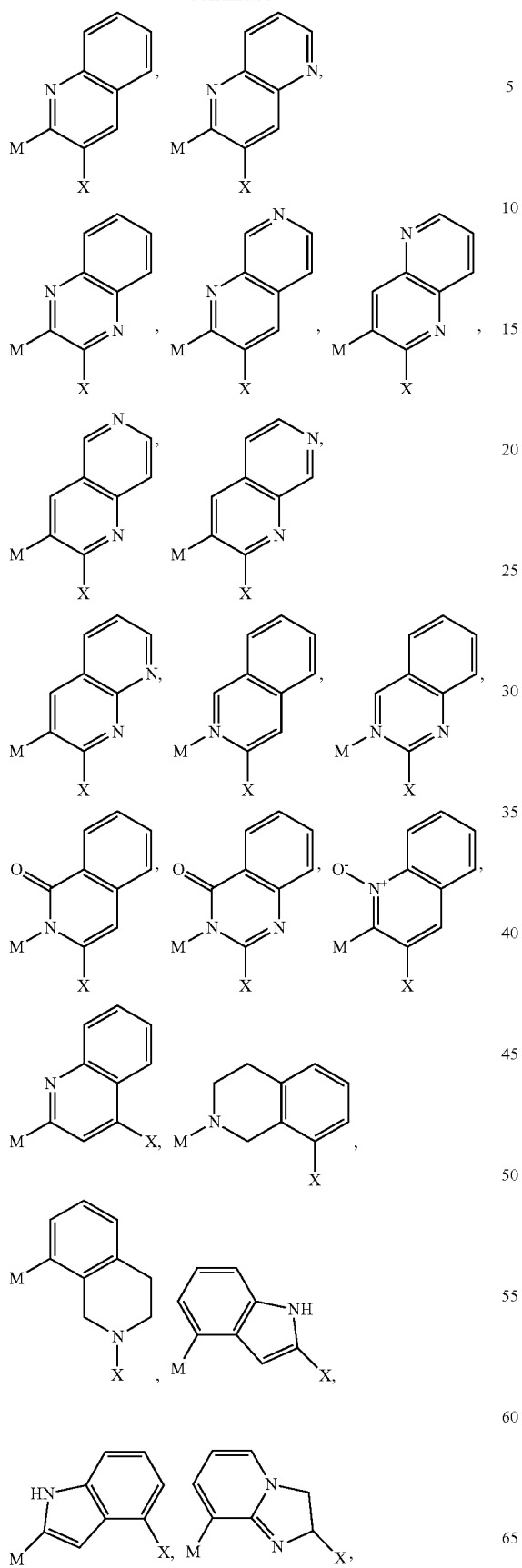
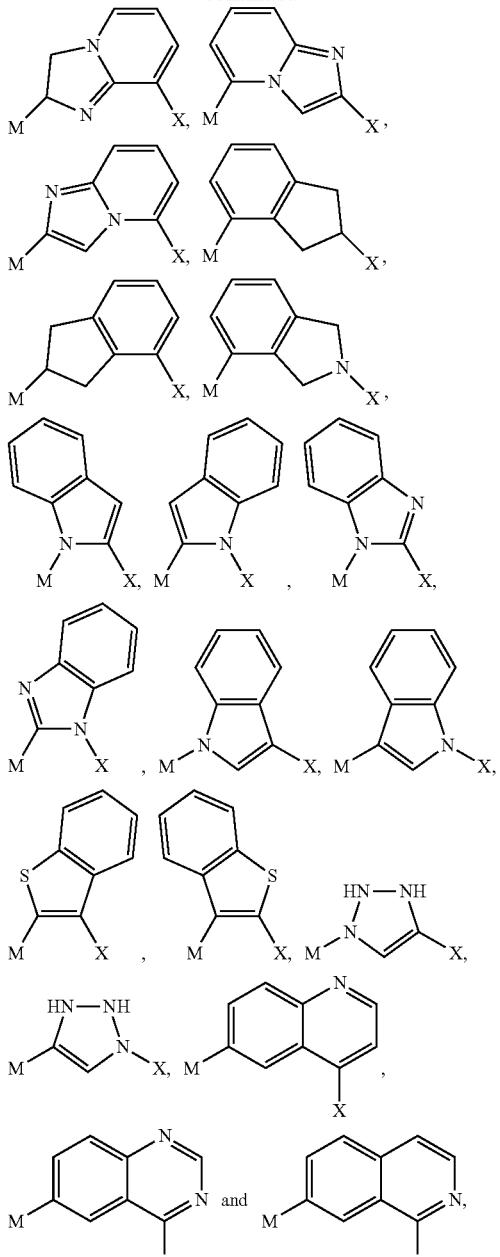
wherein
has 0 to 3 independently selected substituents $R^2$.
In a second aspect of the first embodiment,

is selected from the group consisting of:

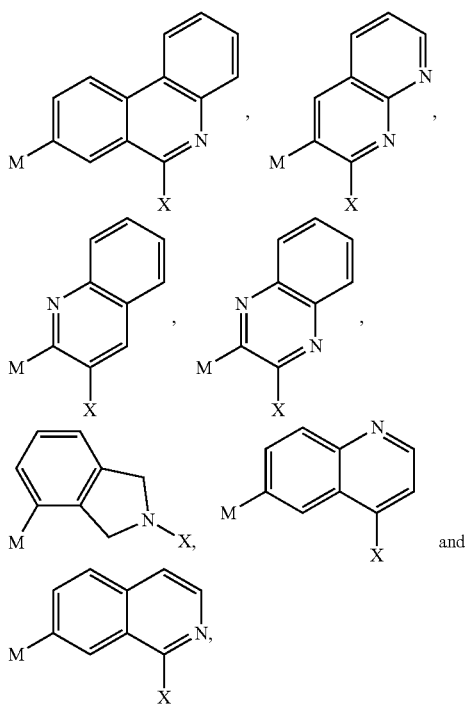

wherein the

has 0 to 3 independently selected substituents $R^2$.
In a third aspect of the first embodiment,

is selected from the group consisting of

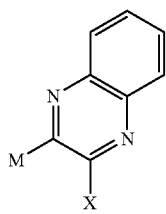

having from 0 to 2 independently selected substituents $R^2$.
In further aspects of the first embodiment,

is substituted by from 0 to 1 $R^2$, wherein $R^2$ is selected from the group consisting of —Br, —Cl, —CN, phenyl, —O-phenyl, —OCF$_3$, —OCH$_3$, —C(O)OH, —CH$_3$ and —C(O)CH$_3$.

In a second embodiment of the invention, X is selected from the group consisting of —C$_{0-5}$ alkylene-O— and —C$_{0-3}$ alkylene-C(O)O—. In particular aspects of the second embodiment, X is selected from the group consisting of —O— and —C(O)O—. In all aspects of this embodiment, all other groups are as provided in the general formula above and/or in the first embodiment.

In a third embodiment of the invention, Y is selected from the group consisting of —OC(O)— and —C(O)—. In this embodiment, all other groups are as provided in the general formula above and/or in the first or second embodiments.

In a fourth embodiment of the invention, M is selected from the group consisting

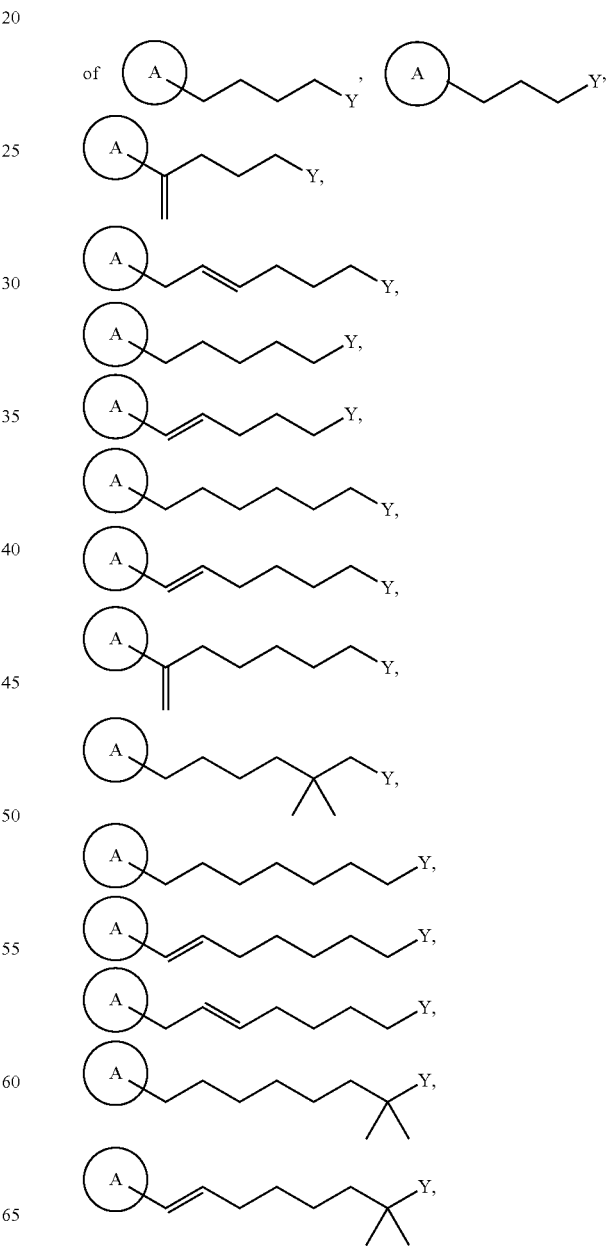

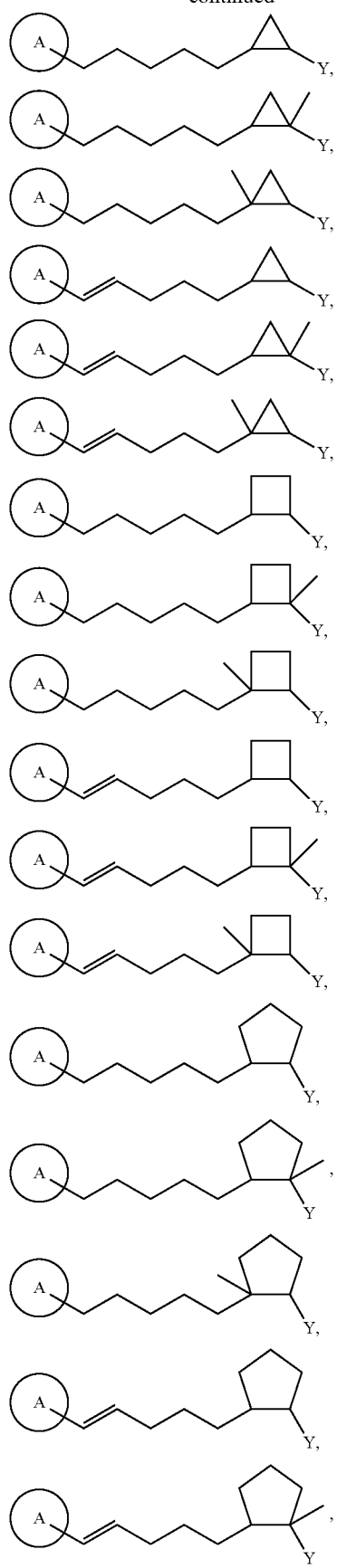
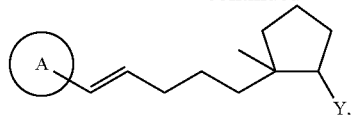
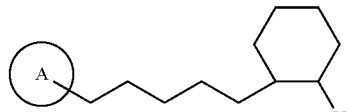
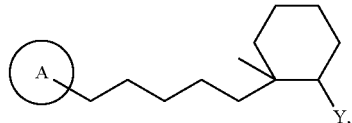
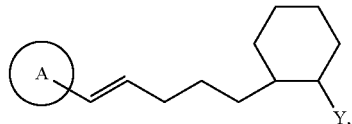
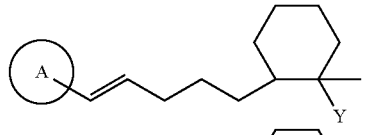
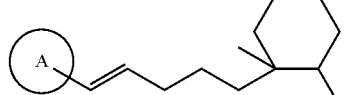
and
In this embodiment and in the aspects of this embodiment described below, all other groups are as provided in the general formula above and/or in the first, second and third embodiments.
In a first aspect of the fourth embodiment of the invention, M is selected from the group consisting of
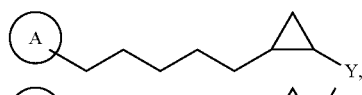
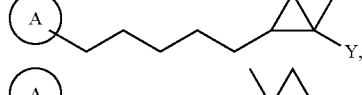
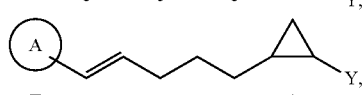
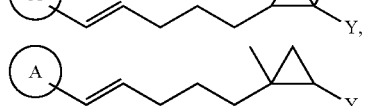
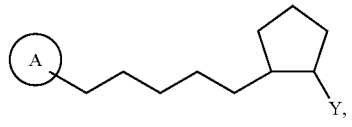

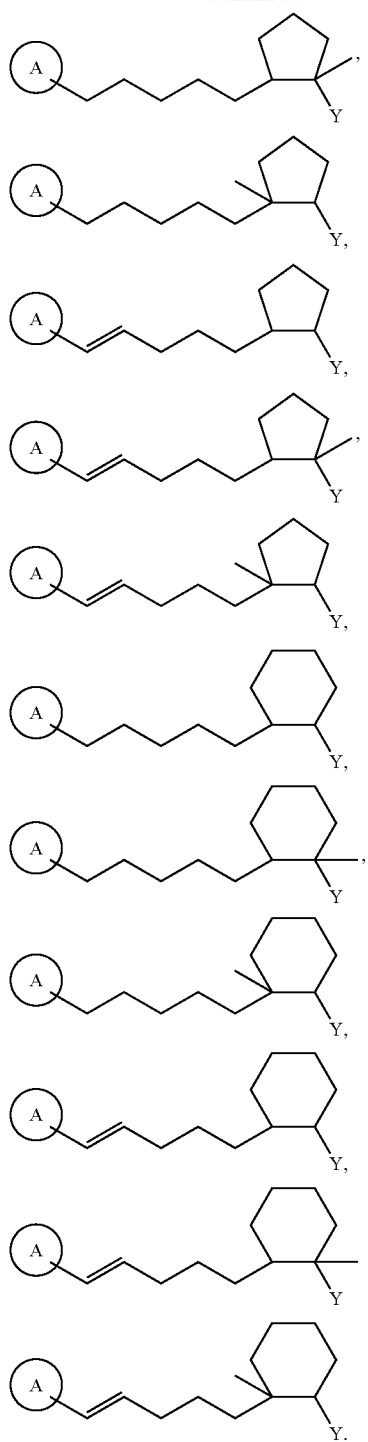

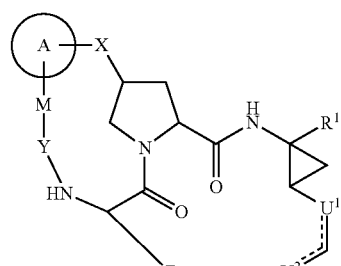

In all aspects of this embodiment, all other groups are as provided in the general formula above and/or in the first, second, third, fourth and fifth embodiments.

A seventh embodiment of the invention is directed to compounds of Formula I:

I and/or pharmaceutically acceptable salts, hydrates or prodrugs thereof, wherein:

A is having from 0 to 1 substituents $R^2$;
$R^2$ is —$OR^3$;
$R^3$ is methyl;
X is —O—;
$R^1$ is

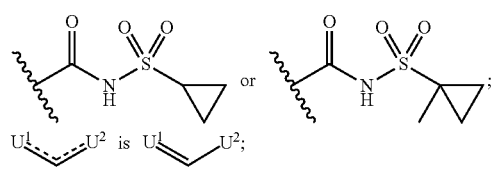

$U^1 \!=\!\!= U^2$ is $U^1 \!=\!\!= U^2$;

In a fifth embodiment of the invention, Z is —$(CH_2)_4$—. In this embodiment, all other groups are as provided in the general formula above and/or in the first, second, third and fourth embodiments.

In a sixth embodiment of the invention, $R^1$ is selected from the group consisting of —$CO_2R^3$ and —$CONR^3SO_2R^6$. In particular aspects of this embodiment, $R^1$ is selected from the group consisting of Z is —(CH$_2$)$_4$—; and
M is

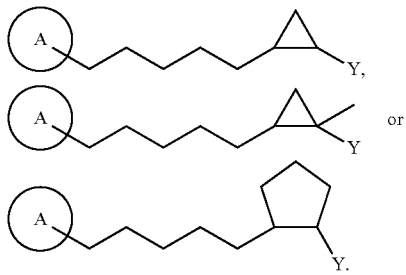

In this embodiment, all other groups are as provided in the general formula above.

In a eighth embodiment of the invention, the compound of the invention is selected from the exemplary species depicted in Examples 1 through 11 shown below.

Other embodiments of the present invention include the following:

(a) A pharmaceutical composition comprising an effective amount of a compound of Formula I and a pharmaceutically acceptable carrier.

(b) The pharmaceutical composition of (a), further comprising at least one additional therapeutic agent independently selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination comprising (i) a compound of Formula I and (ii) at least one additional therapeutic agent independently selected from the group consisting of a HCV antiviral agent, an immunomodulator, and an anti-infective agent; wherein the compound of Formula I and the at least one additional therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof, which comprises administering to the subject an effective amount of a compound of Formula I.

(g) A method of preventing or treating infection by HCV in a subject in need thereof, which comprises administering to the subject an effective amount of a compound of Formula I.

(h) The method of (g), wherein the compound of Formula I is administered in combination with an effective amount of at least one additional therapeutic agent independently selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof, which comprises administering to the subject the pharmaceutical composition of (a), (b), or (c) or the combination of (d) or (e).

(k) A method of preventing or treating infection by HCV in a subject in need thereof, which comprises administering to the subject the pharmaceutical composition of (a), (b), or (c) or the combination of (d) or (e).

(l) The present invention also includes a compound of the present invention (i) for use in, (ii) for use as a medicament for, or (iii) for use in the preparation of a medicament for: (a) inhibiting HCV NS3 protease or (b) preventing or treating infection by HCV. In these uses, the compounds of the present invention can optionally be employed in combination with at least one additional therapeutic agent independently selected from HCV antiviral agents, anti-infective agents, and immunomodulators.

Additional embodiments of the invention include the pharmaceutical compositions, combinations and methods set forth in (a)-(l) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

In the embodiments provided above, it is to be understood that the compound of Formula I may be provided as a free base, a free acid or a pharmaceutically acceptable salt, hydrate or solvate of the compound of Formula I, to the extent that such a free base, a free acid or a pharmaceutically acceptable salt, hydrate or solvate provides a stable compound and is consistent with the description of the embodiments. Thus, any reference to a "compound of Formula I" herein includes reference to the free base form or free acid form, as well as any pharmaceutically acceptable salts, hydrates or solvates, provided that these forms represent a stable compound and are consistent with the description of the embodiments. It is also to be understood that each embodiment may be combined with one or more other embodiments, to the extent that such a combination provides a stable compound and is consistent with the description of the embodiments. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

It is further to be understood that the embodiments of compositions and methods provided as (a) through (k) above are understood to include all embodiments of the compounds, including such embodiments as result from combinations of embodiments.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, the term "alkyl" refers to any linear or branched chain alkyl group having a number of carbon atoms in the specified range. Thus, for example, "C$_{1-6}$ alkyl" (or "C$_1$-C$_6$ alkyl") refers to all of the hexyl alkyl and pentyl alkyl isomers as well as n-, iso-, sec- and tert-butyl, n- and isopropyl, ethyl and methyl. As another example, "C$_{1-4}$ alkyl" refers to n-, iso-, sec- and tert-butyl, n- and isopropyl, ethyl and methyl.

The term "haloalkyl" refers to an alkyl group wherein a hydrogen atom has been replaced by a halogen atom. The term "alkoxy" refers to an "alkyl-O—" group.

The term "alkylene" refers to any linear or branched chain alkylene group (or alternatively "alkanediyl") having a number of carbon atoms in the specified range. Thus, for example, "—C$_{1-6}$ alkylene-" refers to any of the C$_1$ to C$_6$ linear or branched alkylenes. A class of alkylenes of particular interest with respect to the invention is —(CH$_2$)$_{1-6}$—, and sub-classes of particular interest include —(CH$_2$)$_{1-4}$—, —(CH$_2$)$_{1-3}$—, —(CH$_2$)$_{1-2}$—, and —CH$_2$—. Also of interest is the alkylene —CH(CH$_3$)—.

The terms "cycloalkyl" refers to any cyclic ring of an alkane or alkene having a number of carbon atoms in the specified range. Thus, for example, "C$_{3-8}$ cycloalkyl" (or "C$_3$-C$_8$ cycloalkyl") refers to cyclopropyl, cyclobutyl, cyclopentyl, cyclohexyl, cycloheptyl, and cyclooctyl. The term "cycloalkoxy" refers to a "—O-cycloalkyl" group.

The terms "halogen", "halogen atom" and "halo" refer to fluorine, chlorine, bromine and iodine (alternatively referred to as fluoro, chloro, bromo, and iodo).

The term "Het" refers to a 5- to 6-membered saturated cyclic ring having 1 or 2 heteroatoms selected from N, O and S, wherein the ring is optionally substituted with 1 to 3 substituents selected from halo, OR$^3$, SR$^3$, N(R$^3$)$_2$, N(C$_1$-C$_6$ alkyl)O(C$_1$-C$_6$ alkyl), C$_1$-C$_6$ alkyl, C$_1$-C$_6$ haloalkyl, halo(C$_1$-C$_6$ alkoxy), NO$_2$, CN, CF$_3$, SO$_2$(C$_1$-C$_6$ alkyl), S(O)(C$_1$-C$_6$ alkyl), NR$^3$SO$_2$R$^4$, SO$_2$N(R$^4$)$_2$, NHCOOR$^4$, NHCOR$^4$, NHCONHR$^4$, CO$_2$R$^3$, C(O)R$^3$, and CON(R$^3$)$_2$. The oxidized forms of the heteroatoms N and S are included within the scope of the present invention.

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom that results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated (i.e., containing only single bonds) or unsaturated (i.e., containing at least one double and/or triple bonds) and two adjacent carbon atoms are shared by each of the rings in the ring system. A fused bicyclic carbocycle in which all rings are saturated is a saturated bicyclic ring system. A fused bicyclic carbocycle in which at least one ring is unsaturated is an unsaturated bicyclic ring system. Saturated carbocyclic rings are also referred to as cycloalkyl rings (e.g., cyclopropyl, cyclobutyl, etc.). Unless otherwise noted, carbocycle is unsubstituted or substituted with C$_{1-6}$ alkyl, C$_{1-6}$ alkenyl, C$_{1-6}$ alkynyl, aryl, halogen, NH$_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include

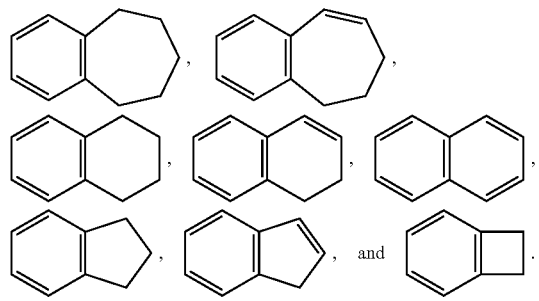

Depicted ring systems include, where appropriate, an indication of the variable to which a particular ring atom is attached. For example, the indole structure

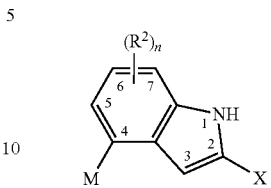

shows ring atom 2 is directly attached to variable X, and ring atom 4 is directly attached to variable M. Variable R$^2$ is shown as a floating variable that can be attached to any ring atom, provided that such attachment results in formation of a stable ring.

The term "aryl" refers to aromatic mono- and poly-carbocyclic ring systems, also referred to as "arenes", wherein the individual carbocyclic rings in the polyring systems are fused or attached to each other via a single bond. Suitable aryl groups include phenyl and naphthyl.

Unless indicated otherwise, the term "heterocycle" (and variations thereof such as "heterocyclic" or "heterocyclyl") broadly refers to (i) a stable 4- to 8-membered, saturated or unsaturated monocyclic ring, (ii) a stable 7- to 12-membered bicyclic ring system, or (iii) a stable 11- to 15-membered tricyclic ring system, wherein each ring in (ii) and (iii) is independent of, or fused to, the other ring or rings and each ring is saturated or unsaturated, and the monocyclic ring, bicyclic ring system or tricyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the bicyclic and tricyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles. Unless expressly stated to the contrary, the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring, a stable 1-5 to 12-membered bicyclic ring system, or a stable 11- to 15-membered tricyclic ring system, which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Unsaturated heterocyclics form another subset of the heterocycles. Unless expressly stated to the contrary, the term "unsaturated heterocyclic" generally refers to a heterocycle as defined above in which the entire ring system (whether mono- or poly-cyclic) is not saturated, i.e., such rings are either unsaturated or partially unsaturated. Unless expressly stated to the contrary, the term "heteroaromatic ring" refers a 5- or 6-membered monocyclic aromatic ring, a 7- to 12-membered bicyclic ring system, or an 11- to 15-membered tricyclic ring system, which consists of carbon atoms and one or more heteroatoms selected from N, O and S. In the case of substituted heteroaromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl, imidazo(2,1-b)(1,3)thiazole, and benzo-1,3-dioxolyl. In certain contexts herein, benzo-1,3-dioxolyl is alternatively referred to as phenyl having as a substituent methylenedioxy attached to 2 adjacent carbon atoms.

Unless otherwise specifically noted as only "unsubstituted" or only "substituted", alkyl, cycloalkyl, aryl and heterocycle groups are unsubstituted or substituted. As used herein, the terms "substituted alkyl", "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group that includes, but is not limited to, halo, $C_1$-$C_{20}$ alkyl, —$CF_3$, —$NH_2$, —$N(C_1$-$C_6$ alkyl)$_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)-S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl. Unless specifically indicated, such substituents themselves are not substituted.

When any variable (e.g., $R^2$, $R^3$ and $R^9$) occurs more than one time in Formula I, any constituent of Formula I, or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

As a result of the selection of substituents and substituent patterns, certain of the compounds of the present invention can have asymmetric centers and can occur as mixtures of stereoisomers, or as individual diastereomers, or enantiomers. All isomeric forms of the claimed compounds, whether isolated or in mixtures, are within the scope of the present invention.

As would be recognized by one of ordinary skill in the art, certain of the compounds of the present invention can exist as tautomers. For the purposes of the present invention a reference to a compound of Formula I is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus, the compounds of this invention are commercial products to be sold for these purposes.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound, salt, hydrate or solvate, and other agents.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means an amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition whose likelihood of occurrence or severity is being reduced. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in such compositions is provided in *Remington's Pharmaceutical Sciences*, 18$^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, RC025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-ata (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN. Levovirin is the L-enantiomer of ribavirin that has shown immunomodulatory activity similar to ribavirin. Viramidine represents an analog of ribavirin disclosed in WO 01/60379. In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB 2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly, and the monophosphate derivative is an inhibitor of IMPDH. Thus, inhibition of IMPDH represents another useful target for the discovery of inhibitors of HCV replication. The compounds of this invention may also be administered in combination with an inhibitor of IMPDH, such as VX-497, which is disclosed in WO 97/41211 and WO 01/00622; another IMPDH inhibitor, such as those disclosed in WO 00/25780; or mycophenolate mofetil (see Anthony C. Allison & Elsie M. Eugui, *Immunosuppressive and other Anthi-Rheumatic Activities of Mycophenolate Mofetil*, 44 (Suppl.) AGENTS ACTION 165 (1993)).

For the treatment of HCV infection, the compounds of the present invention may also be administered in combination with the antiviral agent amantadine (1-aminoadamantane) (see Joel Kirschbaum, *Amantadine in* 12 ANAL. PROFILES DRUG SUBS. 1 (1983)).

For the treatment of HCV infection, the compounds of the present invention may also be administered in combination with the antiviral agent polymerase inhibitor RC128 (Roche).

The compounds of the present invention may also be combined for the treatment of HCV infection with antiviral 2'-C-branched ribonucleosides disclosed in Rogers E. Harry-O'Kuru et al., *A Short, Flexible Route toward* 2'-*C-Branched Ribonucleosides*, 62 J. ORG. CHEM. 1754 (1997); Michael S. Wolfe & Rogers E. Harry-O'Kuru, *A Concise Synthesis of* 2'-*C-Methylribonucleosides*, 36(42) TETRAHEDRON LETT. 7611 (1995); U.S. Pat. No. 3,480,613; WO 01/90121; WO 01/92282; WO 02/32920; WO 2004/002999; WO 2004/003000; and WO 2004/002422; the contents of each of which are incorporated by reference in their entirety. Such 2'-C-branched ribonucleosides include, but are not limited to, 2'-C- methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425; WO 01/79246; WO 02/32920; WO 02/48165; WO 2005/003147 (including RL56, (2'R)-2'-deoxy-2'-fluoro-2'-C-methylcytidine, shown as compounds 3-6 on page 77); WO 01/68663; WO 99/43691; WO 02/18404; US 2005/0038240; WO 2006/021341 (including 4'-azido nucleosides such as RL26, 4'-azidocytidine); US 2002/0019363; WO 02/100415; WO 2003/026589; WO 2003/026675; WO 2003/093290; US 2003/0236216; US 2004/0006007; WO 2004/011478; WO 2004/013300; US 2004/0063658; and WO 2004/028481; the contents of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287; U.S. Pat. No. 6,777,395; WO 02/057425; US 2004/0067901; WO 2003/068244; WO 2004/000858; WO 2004/003138 and WO 2004/007512; the contents of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofaranosyl)-7H-pyrrolo[2,3-d]pyrimidin-4(3H)-one; 2-amino-5-methyl-7-(2-C,2-O-dimethyl-(3-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; and pharmaceutically acceptable salts, solvates and hydrates thereof.

The claimed compounds may also be combined for the treatment of HCV infection with non-nucleoside inhibitors of HCV polymerase such as those disclosed in WO 01/77091; WO 01/47883; WO 02/04425; WO 02/06246; WO 02/20497; WO 2005/016927 (in particular JTK003); and WO 2004/041201 (in particular HCV-796); the contents of each is incorporated herein by reference in its entirety.

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11 carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5- methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts, solvates and hydrates thereof.

The HCV NS3 protease inhibitory activity of the present compounds may be tested using assays known in the art. One such assay is HCV NS3 protease time-resolved fluorescence (TRF) assay as described below and in WO 2006/102087. Other examples of such assays are described in, for example, WO 2005/046712. HCV NS3 protease inhibitors, such as those described herein have a $K_i$ less than 50 μM, such as less than 10 μM, and less than 100 nM. $K_i$ is determined by an NS3 protease assay. The assay is performed in a final volume of 100 μl in assay buffer containing 50 mM HEPES, pH 7.5, 150 mM NaCl, 15% glycerol, 0.15% TRITON X-100, 10 mM DTT, and 0.1% PEG 8000. NS3 protease is preincubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or FUSION fluorophotometer (PERKIN ELMER LIFE AND ANALYTICAL SCIENCES) with excitation at 340 nm and emission at 615 nm with a 400 μs delay. Testing concentrations of different enzyme forms are selected to result in a signal to background ratio (SIB) of 10-30. $IC_{50}$ values are derived using a standard four-parameter fit to the data. $K_i$ values are derived from $IC_{50}$ values using the following formula, $$IC_{50} = K_i(1 + [S]/K_M),  \quad \text{Eqn (1)},$$

where [S] is the concentration of substrate peptide in the reaction and $K_M$ is the Michaelis constant. See Paola Gallinari et al., *Modulation of Hepatitis C Virus NS3 Protease and Helicase Activities through the Interaction with NS4A*, 38 BIOCHEM. 5620 (1999); Paola Gallinari et al., *Multiple Enzymatic Activities Associated with Recombinant NS3 Protein of Hepatitis C Virus*, 72(8) J. VIROLOGY 6758 (1998); Mariana Taliani et al., *A Continuous Assay of Hepatitis C Virus Protease Based on Resonance Energy Transfer Depsipeptide Substrates*, 240 ANAL. BIOCHEM. 60 (1996).

Intermediates C used in the preparation of compounds of the present invention can be prepared as outlined in Schemes 1-3.

In the following schemes, all variables are as defined above unless otherwise indicated. R is $C_{1-6}$ alkyl unless otherwise indicated.

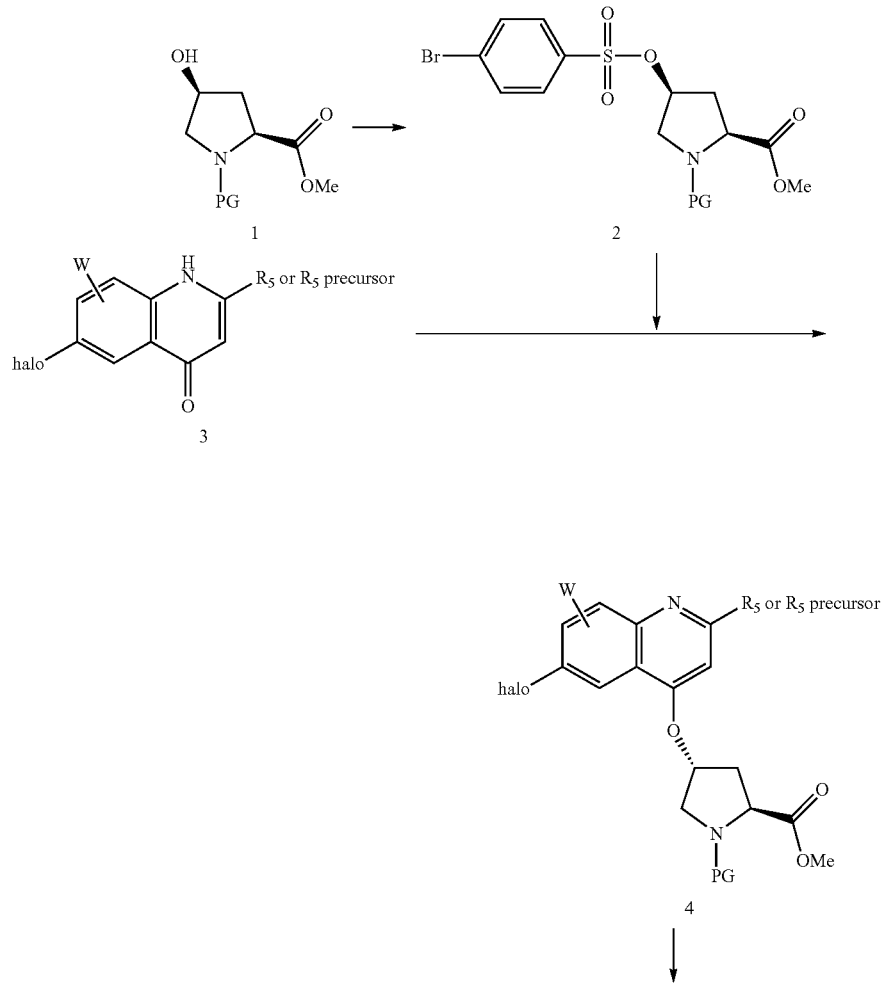

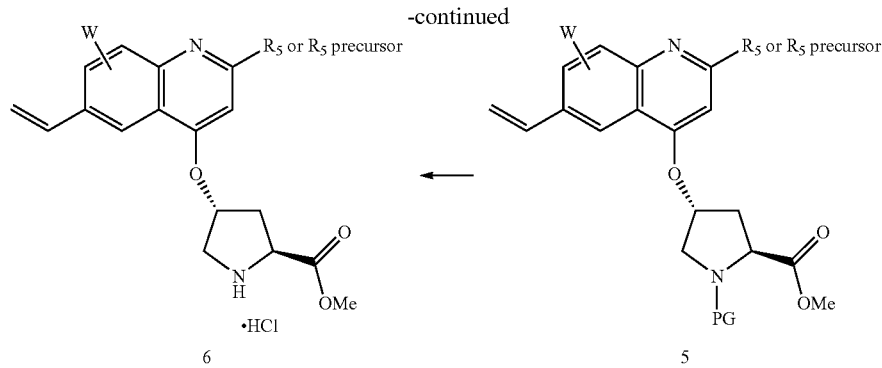

Reaction of an appropriately substituted quinoline derivative 3 with the brosylate of a protected (PG) (e.g., Boc) cis-4-hydroxyproline methyl ester 2 affords the coupled product 4 (Scheme 1). The same intermediates can be prepared by direct reaction of an appropriately substituted quinoline derivative 1 with N-protected cis-4-hydroxyproline methyl ester, utilizing Mitsunobu coupling conditions (see Oyo Mitsunobu, *The Use of Diethyl Azodicarboxylate and Triphenylphosphine in Synthesis and Transformation of Natural Products*, SYNTHESIS 1 (January 1981)). Vinylation of the halo quinoline 4 can then be carried out in a number of different ways including: reaction with vinyltributyltin and an appropriate palladium catalyst (e.g., Pd(PPh₃)₄) in a solvent such as toluene, DMF, DMSO, THF; reaction with potassium vinyltrifluoroborate and an appropriate palladium catalyst (e.g., dichloro[1,1'-bis(diphenylphosphino)ferrocene]palladium (II) dichloromethane adduct), in combination with an amine base such as triethylamine in ethanol or other suitable solvents; and a Heck reaction with ethylene and suitable palladium catalyst in an appropriate solvent. It will be apparent to a person skilled in the art that this vinylation step may also be carried out at alternative points in the synthetic sequences. In the case of a BOC protecting group, the BOC group of 5 can be removed by treatment with acid, such as HCl in a suitable solvent (e.g., dioxane or ethyl acetate) or trifluoroacetic acid either neat or diluted with a solvent such as dichloromethane to provide 6.

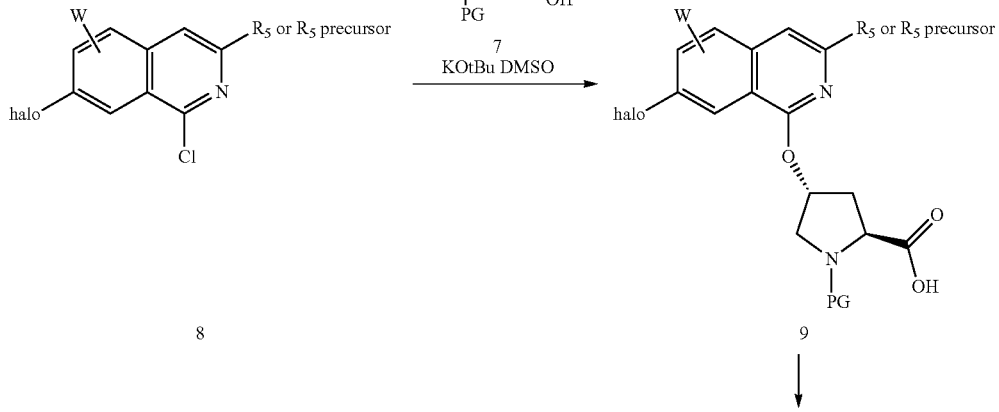

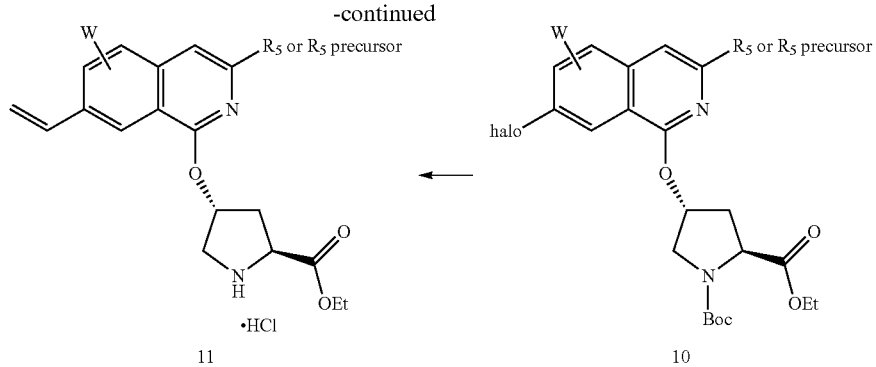

Intermediates C possessing an isoquinolone moiety can be prepared as outlined in Scheme 2. Reaction of N-protected (e.g., BOC) trans 4-hydroxyproline (7) is accomplished by formation of the dianion with base (e.g., KOtBu) in appropriate solvent (DMSO, THF or mixtures thereof) and quenching with a suitably substituted 1-chloroisoquinoline (8). Where PG is BOC, the proline protecting group of the product 9 can be removed and the acid esterified in a single step by treatment with HCl in a suitable alcohol such as ethanol to give, after reformation of the BOC protected amine, 10. Vinylation and removal of the BOC protecting group can then be carried out as described for intermediates in Scheme 1 to provide 11.

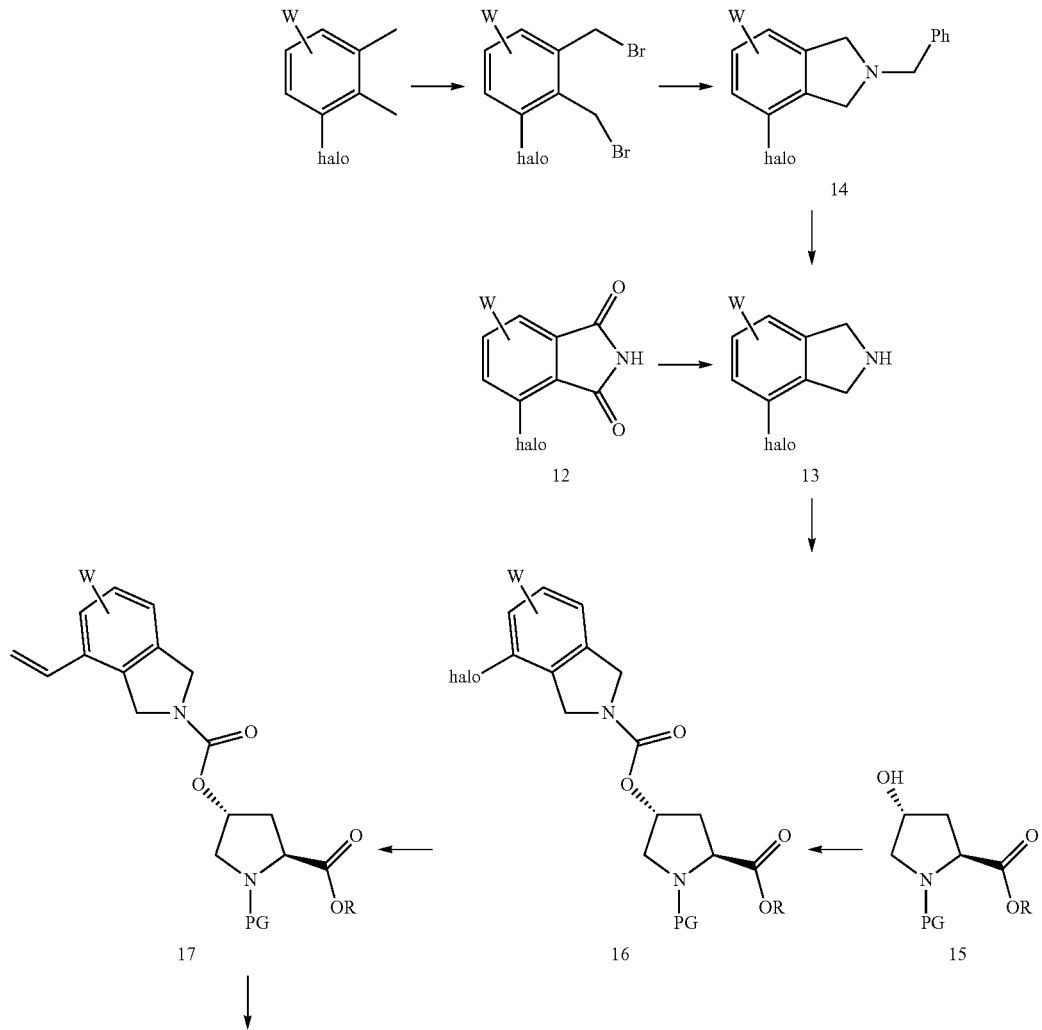

-continued

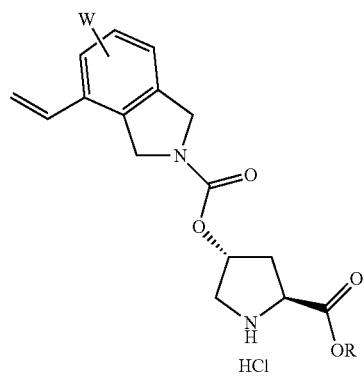

18

Intermediates C containing an isoindoline moiety can be prepared as outlined in Scheme 3. The appropriate haloisoindoline 13 may be formed either by reduction of an appropriate halo substituted phthalimide 12 with, for example, borane, or alternatively an appropriate halo-xylene (e.g., 3-bromo-o-xylene) may be doubly brominated utilizing N-bromosuccinimide and then ring closed by treatment with an amine such as benzylamine in the presence of an organic or inorganic base (e.g., potassium bicarbonate) in a solvent (e.g., acetonitrile). The benzyl group of the resultant isoindoline 14 can then be removed, for example by treatment with α-chloroethylchloroformate (ACE-Cl), followed by treatment with an alcohol (e.g., methanol). The haloisoindoline 13 can then be coupled with N-protected (e.g., BOC) trans-4-hydroxyproline methyl (or ethyl) ester (15), by treatment of the latter with carbonyldiimidazole, phosgene or triphosgene, followed by addition of the haloisoindoline, optionally in the presence of an amine base such as triethylamine. Vinylation of the resulting coupled product 16 to 17 and removal of the proline protecting group to afford 18, can then be carried out as described for the compounds in Scheme 1.

Scheme 4

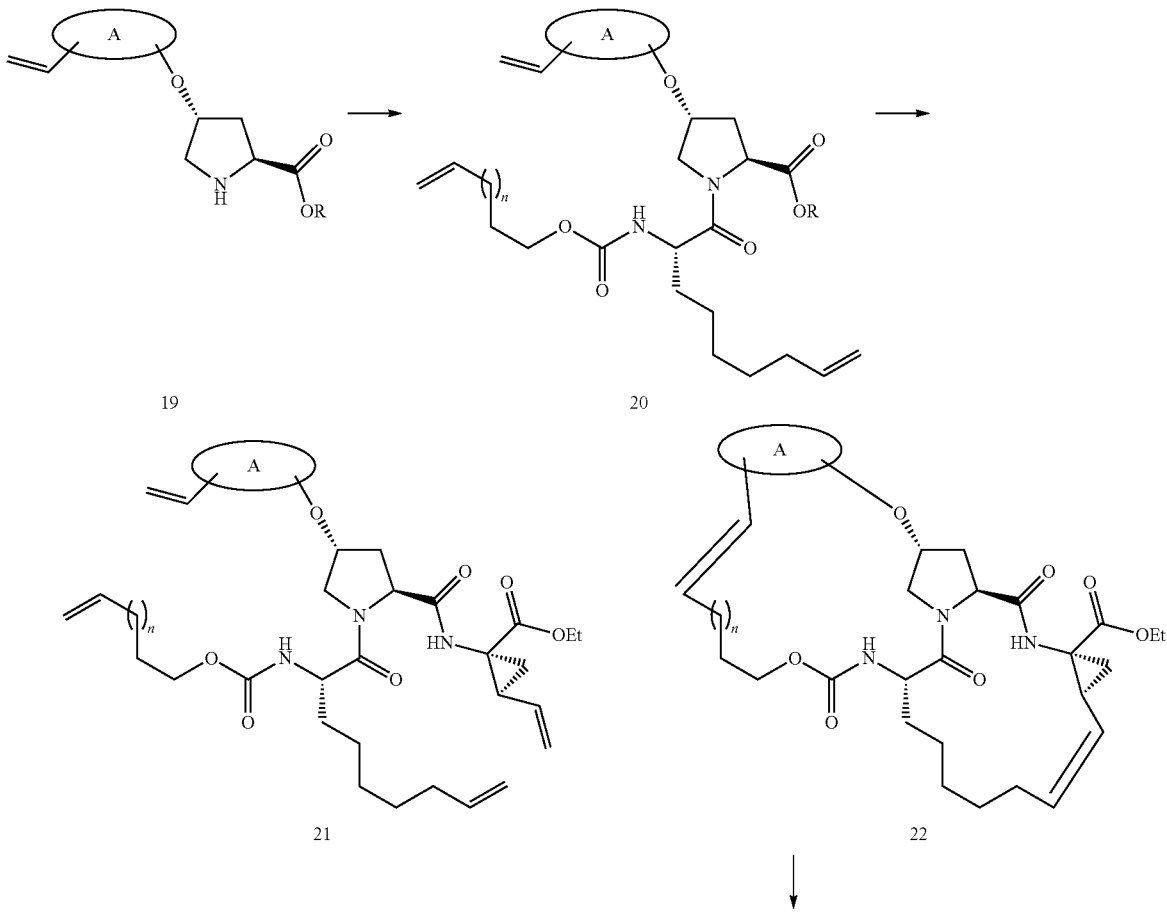

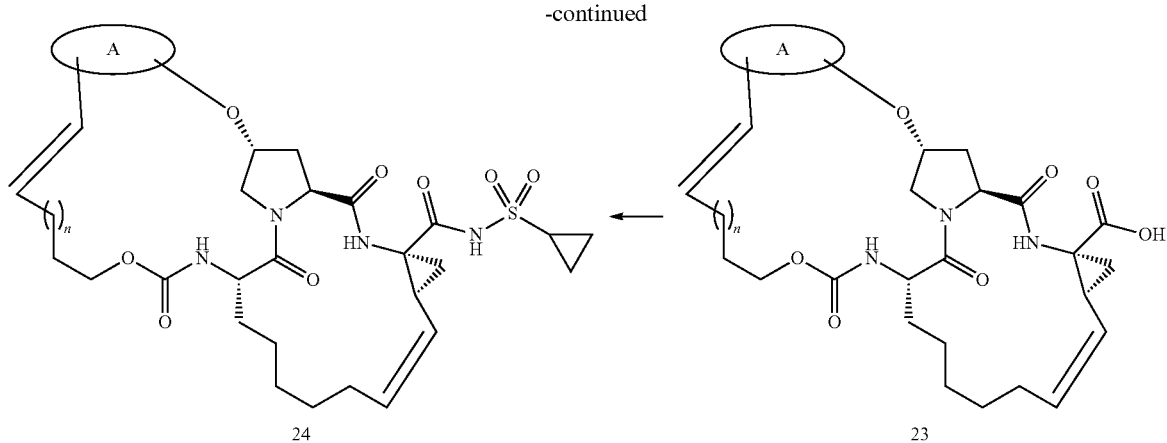

Intermediates C can then be converted to compounds of the present invention by a number of alternative procedures. In the first of these (Scheme 4), an Intermediate C is coupled with an alkenyl carbamate derivative of 2(5)-t-butoxycarbonylamino-non-8-enoic acid (Acme Bioscience Inc.) is coupled with proline derivative 19, using a standard peptide coupling reagent such as EDC, HATU or BOP to give intermediate 20. Hydrolysis of the proline ester and coupling with (1R,2S)-1-amino-2-vinylcyclopropanecarboxylic acid (Pierre J. Beaulieu et al., *Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease*, 70 J. ORG. CHEM. 5869 (2005)) affords tetraolefin 21, which can be subjected to a double ring-closing metathesis reaction to give 22. Bismacrocycle 22, can then be hydrolyzed to give carboxylic acid products 23, which via activation of the carboxylic acid, for example by N,N'-carbonyldiimidazole and reaction with cyclopropyanesulfonamide affords the corresponding acylsulfonamides 24. In a variation on this method, the ester 20 can be hydrolyzed, coupled with (1R,2S)-1-amino-N-(cyclopropylsulfonyl)-2-vinylcyclopropanecarboxamide (WO 2003/099274) and macrocyclized to give directly the acylsulfonamides 24.

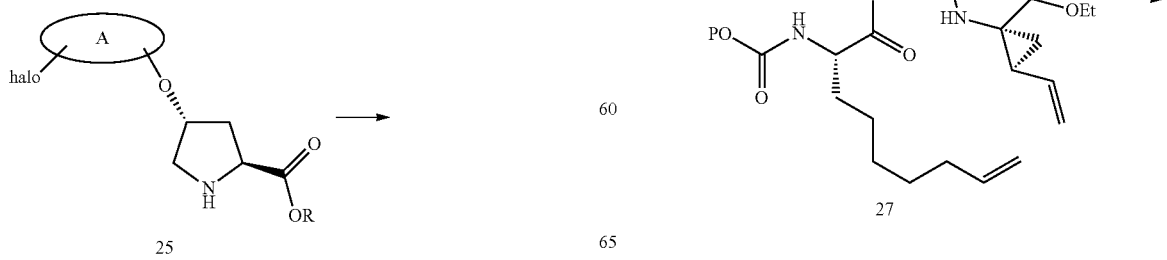

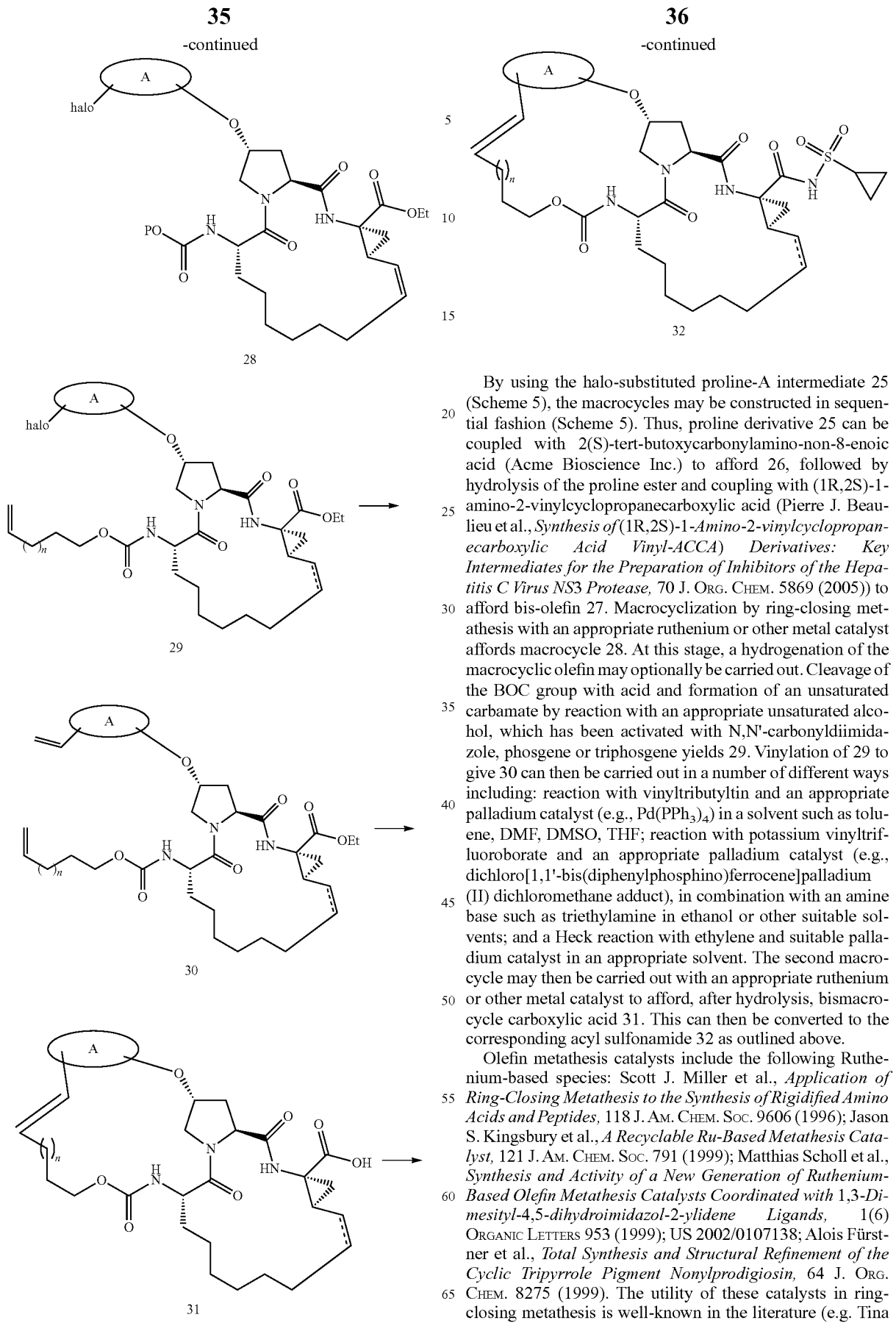

By using the halo-substituted proline-A intermediate 25 (Scheme 5), the macrocycles may be constructed in sequential fashion (Scheme 5). Thus, proline derivative 25 can be coupled with 2(S)-tert-butoxycarbonylamino-non-8-enoic acid (Acme Bioscience Inc.) to afford 26, followed by hydrolysis of the proline ester and coupling with (1R,2S)-1-amino-2-vinylcyclopropanecarboxylic acid (Pierre J. Beaulieu et al., *Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease*, 70 J. ORG. CHEM. 5869 (2005)) to afford bis-olefin 27. Macrocyclization by ring-closing metathesis with an appropriate ruthenium or other metal catalyst affords macrocycle 28. At this stage, a hydrogenation of the macrocyclic olefin may optionally be carried out. Cleavage of the BOC group with acid and formation of an unsaturated carbamate by reaction with an appropriate unsaturated alcohol, which has been activated with N,N'-carbonyldiimidazole, phosgene or triphosgene yields 29. Vinylation of 29 to give 30 can then be carried out in a number of different ways including: reaction with vinyltributyltin and an appropriate palladium catalyst (e.g., Pd(PPh$_3$)$_4$) in a solvent such as toluene, DMF, DMSO, THF; reaction with potassium vinyltrifluoroborate and an appropriate palladium catalyst (e.g., dichloro[1,1'-bis(diphenylphosphino)ferrocene]palladium (II) dichloromethane adduct), in combination with an amine base such as triethylamine in ethanol or other suitable solvents; and a Heck reaction with ethylene and suitable palladium catalyst in an appropriate solvent. The second macrocycle may then be carried out with an appropriate ruthenium or other metal catalyst to afford, after hydrolysis, bismacrocycle carboxylic acid 31. This can then be converted to the corresponding acyl sulfonamide 32 as outlined above.

Olefin metathesis catalysts include the following Ruthenium-based species: Scott J. Miller et al., *Application of Ring-Closing Metathesis to the Synthesis of Rigidified Amino Acids and Peptides*, 118 J. AM. CHEM. SOC. 9606 (1996); Jason S. Kingsbury et al., *A Recyclable Ru-Based Metathesis Catalyst*, 121 J. AM. CHEM. SOC. 791 (1999); Matthias Scholl et al., *Synthesis and Activity of a New Generation of Ruthenium-Based Olefin Metathesis Catalysts Coordinated with 1,3-Dimesityl-4,5-dihydroimidazol-2-ylidene Ligands*, 1(6) ORGANIC LETTERS 953 (1999); US 2002/0107138; Alois Fürstner et al., *Total Synthesis and Structural Refinement of the Cyclic Tripyrrole Pigment Nonylprodigiosin*, 64 J. ORG. CHEM. 8275 (1999). The utility of these catalysts in ring-closing metathesis is well-known in the literature (e.g. Tina M. Trnka Robert H. Grubbs, *The Development of*

$L_2X_2Ru=CHR$ Olefin Metathesis Catalysts: An Organometallic Success Story, 34 ACC. CHEM. RES. 18 (2001)).

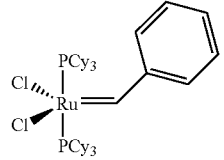
F

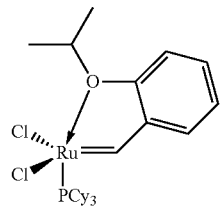
G

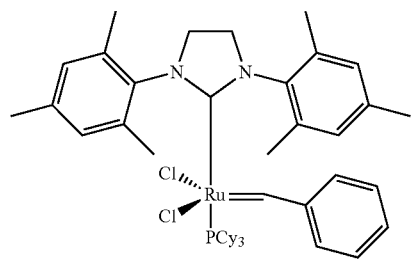
H

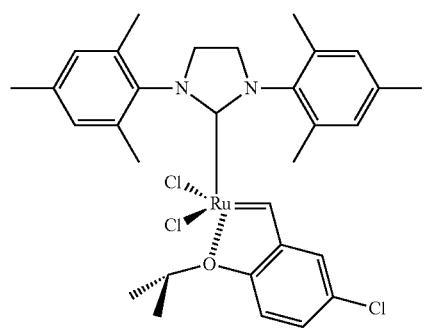
J

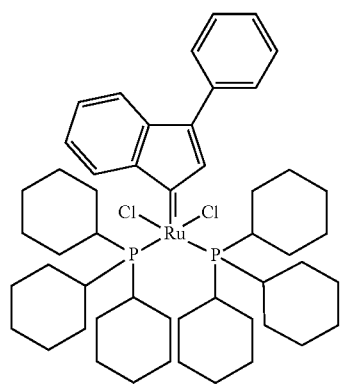
K

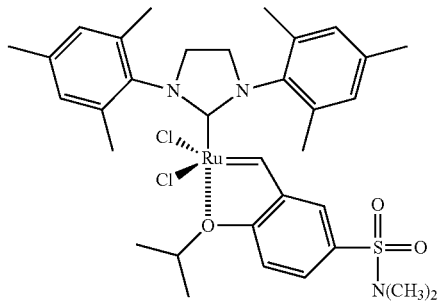
L

Zhan ruthenium metathesis catalyst RC-303
(Zhan catalyst 1B, RC-303, Zannan Pharma Ltd.)

LIST OF ABBREVIATIONS

BHT Butylated hydroxytoluene
$BOC_2O$ Di-tert-butyl dicarbonate
BOP Benzotriazole-1-yl-oxy-tris-(dimethylamino)-phosphonium hexafluorophosphate
Brosyl 4-Bromobenzenesulfonyl
Brosyl chloride 4-Bromobenzenesulfonyl chloride
CDI N,N'-Carbonyl diimidazole
$CH_3CN$ Acetonitrile
$Cs_2CO_3$ Cesium carbonate
CsF Cesium fluoride
DBU 1,8-Diazabicyclo[5.4.0]undec-7-ene
DCC Dicyclohexylcarbodiimide
DCE Dichloroethane
DCM Dichloromethane
DIAD Diisopropyl azodicarboxylate
DIPEA Diisoproylethylamine
DMAP 4-Dimethylamino pyridine
DMF Dimethylformamide
DMSO Dimethyl sulfoxide
EDC N-(3-Dimethylaminopropyl)-N'-ethylcarbodiimide
$Et_3N$ Triethylamine
$Et_2O$ Diethyl ether
EtOAc Ethyl acetate
EtOH Ethanol
HATU O-(7-Azabenzotriazol-1-yl)-N,N,N',N'-tetramethyluronium hexafluorophosphate
HBr Hydrobromic acid
HCl Hydrochloric acid
$H_2O$ Water
HOAc Acetic acid
HOAt 1-Hydroxy-7-azabenzotriazole
$KBH_4$ Potassium borohydride
$K_2CO_3$ Potassium carbonate
$KHSO_4$ Potassium bisulfate
LiOH Lithium hydroxide
MeCN Acetonitrile
MeOH Methanol
$MgSO_4$ Magnesium sulfate
MTBE Methyl tert-butyl ether
$N_2$ Nitrogen gas or atmosphere
$Na_2SO_4$ Sodium sulfate
$NaHCO_3$ Sodium bicarbonate
NaOH Sodium hydroxide
$NH_4Cl$ Ammonium chloride
$NH_4OH$ Ammonium hydroxide
NMP N-Methyl pyrrolidinone
Pd/C Palladium on carbon Pd(PPh₃)₄ Tetrakis(triphenylphosphine)palladium (0)
PhMe Toluene
PPh₃ Triphenylphosphine
PPTS Pyridium p-toluenesulfonate
RT Room temperature
SOCl₂ Thionyl chloride
SiO₂ Silica or silica gel TBTU O-Benzotriazol-1-yl-N,N,N,N'-tetramethyluronium tetrafluoroborate
TFA Trifluoroacetic acid
THF Tetrahydrofuran Synthesis of Intermediates Intermediates A

| Intermediate # | Structure | Name | Literature Reference |
|---|---|---|---|
| A1 | 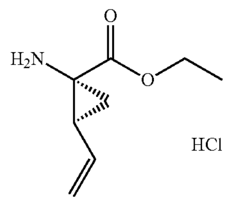 | Ethyl (1R,2S)-1-amino-2-vinylcyclopropanecarboxylate hydrochloride | U.S. Pat. No. 6,323,180 |

Intermediates B

| Intermediate # | Structure | Name | Literature Reference |
|---|---|---|---|
| B1 | 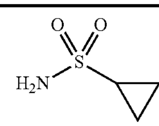 | cyclopropanesulfonamide | WO 20080502 Commercially available from APAC Pharm # 816686 |
| B2 | 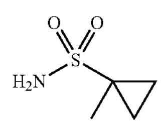 | 1-methylcyclopropanesulfonamide | WO 20080502 Commercially available from Asta Tech # 64790 |

Intermediates C

| Intermediate # | Structure | Name | Literature Reference |
|---|---|---|---|
| C1 | 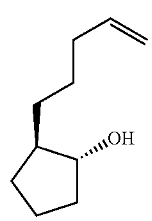 | (1R,2R)-2-(pent-4-en-1-yl)cyclopentanol | WO 2008057209 |
| C2 | 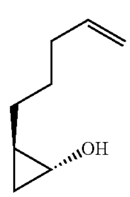 | (1R,2R)-2-(pent-4-en-1-yl)cyclopropanol | WO 2008057209 |

Intermediate C3: (1R,2R)-1-methyl-2-(pent-4-en-1-yl)cyclopropanol

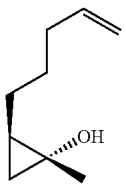

To a solution of 1,6-heptadiene (19.65 g, 204 mmol), in THF (341 ml) was added EtOAc (6.67 ml, 68.1 mmol), and chlorotitanium triisopropoxide (68.1 ml, 68.1 mmol). Cyclohexylmagnesium chloride (2M, 153 ml, 306 mmol) was then added slowly over 2 hours. After an additional 1 hour of stirring at RT, the reaction mixture was filtered through CELITE. The filtrate was then concentrated in vacuo and purified on $SiO_2$ (15% EtOAc/hexanes) to yield the title compound as a mixture of enantiomers. To a solution of the enantiomers (5.5 g, 39.2 mmol) in anhydrous DCM, at 0° C. and under $N_2$, was added $Et_3N$ (10.9 mL, 78 mmol) and 4-nitrobenzoyl chloride (8.7 g, 47.1 mmol). The reaction was stirred for 2 hours, diluted with $H_2O$ (70 mL) and extracted with DCM (3×100 mL). The combined organic layer was dried over $Na_2SO_4$, filtered and concentrated in vacuo. The residue was purified on $SiO_2$ (gradient elution, 0 to 50% EtOAc in hexane) to yield (1R,2R and 1S,2S)-1-methyl-2-(pent-4-en-1-yl)cyclopropyl 4-nitrobenzoate. The benzoate enantiomers (12 g, 41.5 mmol) were separated by chiral chromatography on an AD-H column, eluting with 10% $CO_2$ in MeOH. The desired peak fractions were concentrated to give (1R,2R)-1-methyl-2-(pent-4-en-1-yl)cyclopropyl 4-nitrobenzoate. To a solution of (1R,2R)-1-methyl-2-(pent-4-en-1-yl)cyclopropyl 4-nitrobenzoate (4.87 g, 16.83 mmol) in MeOH (67 mL) was added $K_2CO_3$ (4.65 g, 33.7 mmol). The mixture was stirred for 1 hour, filtered, and concentrated in vacuo. The material was purified on $SiO_2$ (gradient elution, 0-50% ether/hexanes) to give the title compound. $^1$H NMR (500 MHz) ($CDCl_3$) δ 5.82 (m, 1H), 4.99 (m, 2H), 2.09 (m, 2H), 1.78 (s, 1H), 1.55 (m, 2H), 1.41 (s, 3H), 1.32 (m, 1H), 1.14 (m, 1H), 0.97 (m, 1H), 0.84 (m, 1H), 0.06 (m, 1H).

Intermediates D

Intermediate D1: 1-[({[(1R,2R)-2-(pent-4-en-1-yl)cyclopentyl]oxy}carbonyl)oxy]pyrrolidine-2,5-dione

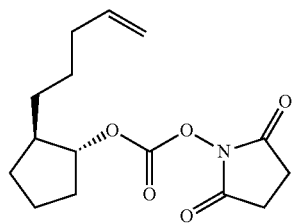 [SMILES: C=CCCC[C@@H]1CCC[C@H]1OC(=O)ON1C(=O)CCC1=O]

To a solution of Intermediate C1 (22 g, 143 mmol) in MeCN (285 ml) was added N,N'-disuccinimidyl carbonate (43.8 g, 171 mmol) followed by $Et_3N$ (59.6 ml, 428 mmol). The mixture was then stirred for 20 hours at 40° C. After 45 minutes, an additional portion of N'-disuccinimidyl carbonate (10 g, 39 mmol) was added and stirring was continued for 5.5 hours. The mixture was concentrated in vacuo and purified on $SiO_2$ (gradient elution, 0% to 70% EtOAc in hexanes) to yield the title compound. $^1$H NMR (500 MHz) ($CDCl_3$) δ 5.80 (m, 1H), 5.0 (m, 2H), 4.83 (m, 1H), 2.83 (s, 4H), 1.8-2.1 (m, 6H), 1.70 (m, 2H), 1.43 (m, 2H), 1.26 (m, 2H).

The following Intermediates (D2, D3) were prepared using the chemistry described for the preparation of Intermediate D1, by utilizing the appropriate alcohol.

| Intermediate # | Alcohol | Structure | Name |
|---|---|---|---|
| D2 | C2 | 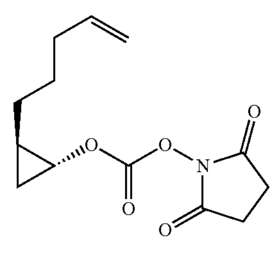 [SMILES: C=CCCC[C@@H]1C[C@H]1OC(=O)ON1C(=O)CCC1=O] | 1-[({[(1R,2R)-2-(pent-4-en-1-yl)cyclopropyl]oxy}carbonyl)oxy]pyrrolidine-2,5-dione |
| D3 | C3 | 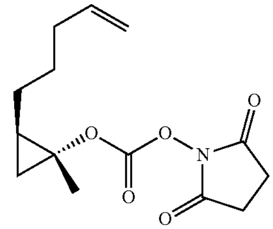 [SMILES: C=CCCC[C@@H]1C[C@@]1(C)OC(=O)ON1C(=O)CCC1=O] | 1-[({[(1R,2R)-1-methyl-2-(pent-4-en-1-yl)cyclopropyl]oxy}carbonyl)oxy]pyrrolidine-2,5-dione |

Intermediates E

Intermediate E1: 1-tert-butyl 2-methyl (2S,4R)-4-[(3-chloro-7-methoxyquinoxalin-2-yl)oxy]pyrrolidine-1,2-dicarboxylate

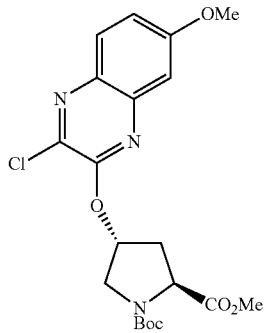 [SMILES: COC(=O)[C@@H]1C[C@@H](Oc2nc3cc(OC)ccc3nc2Cl)CN1C(=O)OC(C)(C)C]

Step 1: 6-methoxyquinoxaline-2,3-diol

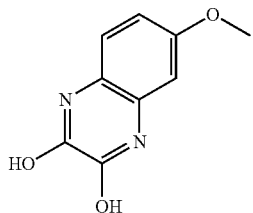

A suspension of 4-methoxybenzene-1,2-diamine dihydrochloride in diethyl oxalate (8 eq) was treated with $Et_3N$ (2 eq) and then heated at 150° C. for 2 hours. The mixture was cooled and filtered, and then the collected solid was washed with $H_2O$ and EtOH. The residue was dried to give the title compound (69%). MS (ES$^+$) m/z 193 (M+H)$^+$

Step 2: 3-chloro-7-methoxyquinoxalin-2-ol

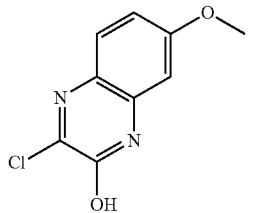

A solution (1.53M) of the product of step 1 in DMF was treated with $SOCl_2$ (1 eq) and heated at 110° C. After 1.5 hours, the reaction mixture was cooled and poured into aqueous HCl (1 N). The resulting precipitate was filtered and washed with $H_2O$ and $Et_2O$. The dried solid contained predominantly the title compound as a mixture with 6-methoxyquinoxaline-2,3-diol and 2,3-dichloro-6-methoxyquinoxaline. This material was used directly in the subsequent step. MS (ES$^+$) m/z 211 (M+H)$^+$

Step 3: 1-tert-butyl 2-methyl (2S,4R)-4-[(3-chloro-7-methoxyquinoxalin-2-yl)oxy]pyrrolidine-1,2-dicarboxylate

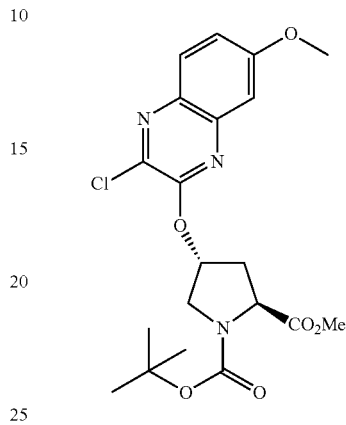

A solution (0.35M) of the product of step 2 in NMP was treated with $Cs_2CO_3$ (1.5 eq) and 1-tert-butyl 2-methyl (2S,4S)-4-{[(4-bromophenyl)sulfonyl]oxy}pyrrolidine-1,2-dicarboxylate (1.1 eq). The resulting mixture was stirred at 50° C. for 18 hours, then a further portion (0.1 eq) of 1-tert-butyl 2-methyl (2S,4S)-4-{[(4-bromophenyl)sulfonyl]oxy}pyrrolidine-1,2-dicarboxylate was added. After stirring for 2 hours, the mixture was cooled and diluted with $H_2O$ and EtOAc. The organic phases were washed with aqueous HCl (1 N), saturated aqueous $NaHCO_3$ and brine. The dried organic phase was concentrated to a residue that was purified by flash-chromatography (0-60% EtOAc/petroleum ether) to give the title compound (35% for two steps) as a solid. MS (ES$^-$) m/z 438 (M+H)$^+$

Intermediate E2: 1-tert-butyl 2-methyl (2S,4R)-4-[(3-chloroquinoxalin-2-yl)oxy]pyrrolidine-1,2-dicarboxylate

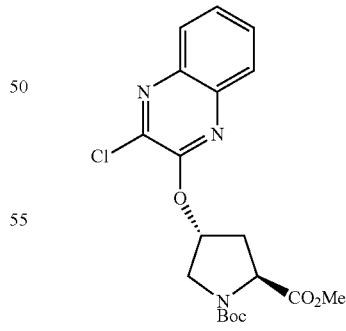

A solution of 3-chloroquinoxalin-2-ol (1.44 g, 7.97 mmol) (Yusuf Ahmad et al., *Quinoxaline Derivatives, XI. The Reaction of Quinoxaline 1,4-Dioxide and Some of Its Derivatives with Acetyl Chloride*, 38(12) J. ORG. CHEM. 2176 (1973)) and 1-tert-butyl 2-methyl (2S,4S)-4-hydroxypyrrolidine-1,2-dicarboxylate (2.05 g, 8.37 mmol) in THF (190 ml) was cooled to 0° C., then treated with $PPh_3$ (2.51 g, 9.57 mmol). DIAD (1.86 ml, 9.57 mmol) was added dropwise, and the mixture was stirred at 20° C. for 1 hour. After evaporation of the volatiles, the residue was purified on SiO$_2$ (gradient elution, 0-70% EtOAc/petroleum ether) to afford the title compound (2.5 g, 77%). LCMS (ES+) m/z 408 (M+H)$^+$

Example 1

(3R,20R,24R,28S,34Z,36S,38R,41S)—N-(Cyclopropylsulfonyl)-9-methoxy-26,40,42-trioxo-4,25-dioxa-1,6,13,27,39-pentaazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide

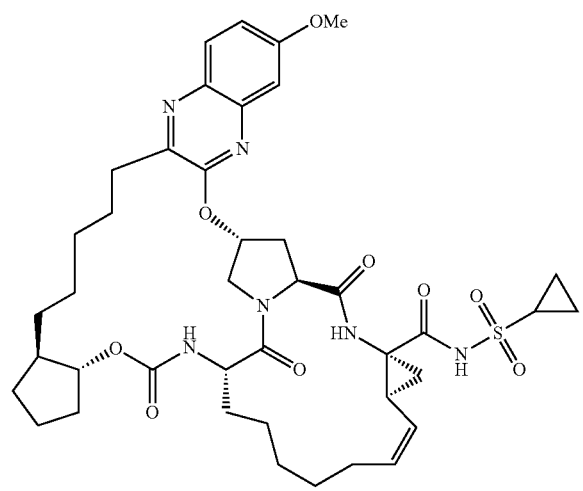 [SMILES: COc1ccc2nc3c(nc2c1)O[C@@H]1C[C@H]2C(=O)N[C@]4(C(=O)NS(=O)(=O)C5CC5)C[C@H]4/C=C\CCCCC[C@H](NC(=O)O[C@@H]4CCC[C@H]4CCCCC3)C(=O)N2C1]

Step 1: tert-Butyl (2S,4R)-4-[(3-chloro-7-methoxyquinoxalin-2-yl)oxy]-2-{[(1R,2S)-2-ethenyl-1-(ethoxycarbonyl)cyclopropyl]carbamoyl}pyrrolidine-1-carboxylate

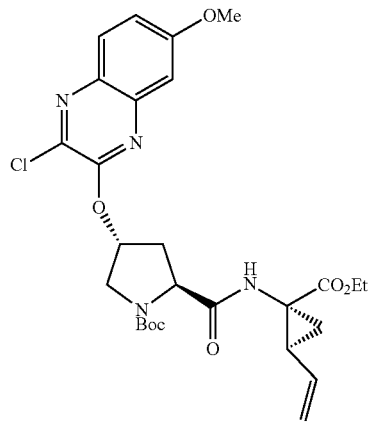 [SMILES: C=C[C@@H]1C[C@]1(NC(=O)[C@@H]1C[C@@H](Oc2nc3cc(OC)ccc3nc2Cl)CN1C(=O)OC(C)(C)C)C(=O)OCC]

To a solution of Intermediate E1 (12 g, 27.4 mmol) in THF (50 mL), MeOH (12.5 mL), and H$_2$O (25 mL) was added LiOH (3.28 g, 137 mmol). After 1 hour, the mixture was extracted with EtOAc and 1 N HCl. The organic layer was washed with brine, dried over Na$_2$SO$_4$, and concentrated in vacuo to yield (4R)-1-(tert-butoxycarbonyl)-4-[(3-chloro-7-methoxyquinoxalin-2-yl)oxy]-L-proline, which was dissolved in DMF (50 mL). To this solution was added Intermediate A1 (6 g, 31.3 mmol), DIPEA (14.3 mL, 82 mmol), and HATU (11.5 g, 30.1 mmol). After 1 hour, the mixture was extracted with Et$_2$O/EtOAc and 0.5 N HCl. The organic layer was washed with brine, dried over Na$_2$SO$_4$, and concentrated in vacuo. The crude material was purified on SiO$_2$ (gradient elution, 5% to 100% EtOAc in hexanes) to yield the title compound. LRMS (ESI) m/z 561.5 [(M+H)$^+$; calculated for C$_{27}$H$_{34}$ClN$_4$O$_7$ 561.2].

Step 2: Ethyl (1R,2S)-1-({(4R)-1-{(2S)-2-[(tert-butoxycarbonyl)amino]non-8-enoyl}-4-[(3-chloro-7-methoxyquinoxalin-2-yl)oxy]-L-prolyl}amino)-2-ethenylcyclopropanecarboxylate

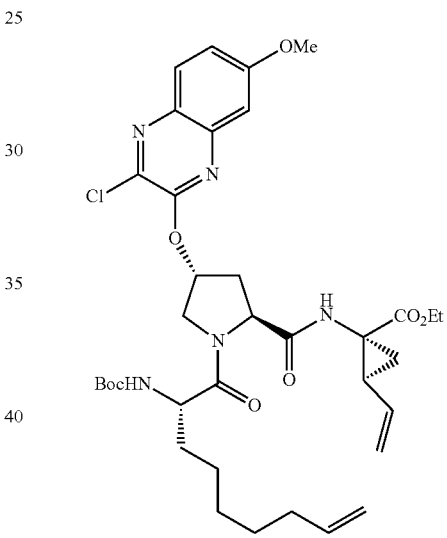

To the product from step 1 (66.8 g, 119 mmol) was added HCl in dioxane (4M, 595 mL, 2381 mmol). The mixture was stirred for 1 hour, diluted with Et$_2$O (500 mL), and filtered. The collected solid was washed with Et$_2$O and dried under vacuum to yield ethyl (1R,2S)-1-({(4R)-4-[(3-chloro-7-methoxyquinoxalin-2-yl)oxy]-L-prolyl}amino)-2-ethenylcyclopropanecarboxylate hydrochloride, which was then added to DMF (226 mL). To this mixture was added (2S)-2-[(tert-butoxycarbonyl)amino]non-8-enoic acid (32.9 g, 121 mmol) (commercially available from Synthetech as the dicyclohexylamine salt), DIPEA (59.3 mL, 340 mmol), and HATU (47.3 g, 125 mmol). After 1 hour, the mixture was extracted with EtOAc and 0.5N HCl. The organic layer was washed with brine, dried over MgSO$_4$, and concentrated in vacuo. The crude material was purified on silica (gradient elution, 0% to 100% EtOAc in hexanes) to yield the title compound. LRMS (ESI) m/z 714.5; (M+H)$^+$; calculated for C$_{36}$H$_{49}$ClN$_5$O$_8$ 714.3.

Step 3: Ethyl (1R,2S)-1-[(tert-butoxycarbanyl){(4R)-1-{(2S)-2-[(tert-butoxycarbanyl)amino]non-8-enoyl}-4-[(3-chloro-7-methoxyquinoxalin-2-yl)oxy]-L-prolyl}amino]-2-ethenylcyclopropanecarboxylate

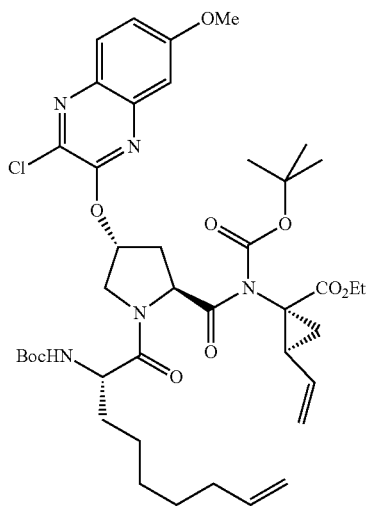 [SMILES: C=CCCCCC[C@H](NC(=O)OC(C)(C)C)C(=O)N1C[C@H](Oc2nc3cc(OC)ccc3nc2Cl)C[C@H]1C(=O)N(C(=O)OC(C)(C)C)[C@]1(C(=O)OCC)C[C@H]1C=C]

To a solution of the product from step 2 (54.6 g, 76 mmol) and DMAP (2.80 g, 22.93 mmol) in EtOAc (648 ml) at 0° C. was added BOCA) (26.6 ml, 115 mmol) dropwise in 60 mL EtOAc. The mixture was warmed to RT, stirred for 18 hours, and extracted with EtOAc and $H_2O$. The organic layer was dried over $MgSO_4$, and concentrated in vacuo. The crude material was then purified on $SiO_2$ (gradient elution, 0-70% EtOAc/hexanes) to yield the title compound. LRMS (ESI) m/z 814.6 [(M+H)$^+$; calculated for $C_{41}H_{57}ClN_5O_{10}$ 814.4].

Step 4: 15-tert-Butyl 14a-ethyl (2R,6S,12Z,13aS,14aR,16aS)-6-[(tert-butoxycarbanyl)amino]-2-[(3-chloro-7-methoxyquinoxalin-2-yl)oxy]-5,16-dioxo-2,3,6,7,8,9,10,11,13a,14,16,16a-dodecahydrocyclopropa[e]pyrrolo[1,2-a][1,4]diazacyclopentadecine-14a,15(1H,5H)-dicarboxylate

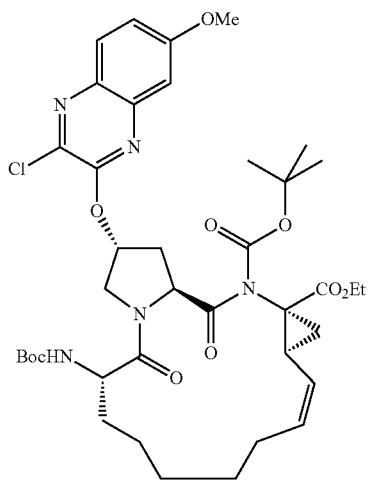 [SMILES: CCOC(=O)[C@@]12C[C@H]1/C=C\CCCCC[C@H](NC(=O)OC(C)(C)C)C(=O)N1C[C@H](Oc3nc4cc(OC)ccc4nc3Cl)C[C@H]1C(=O)N2C(=O)OC(C)(C)C]

To a degassed solution of the product from step 3 (32.1 g, 39.4 mmol) in DCE (1.6 L) at 75° C. was added Zhan 1b catalyst (435 mg, 0.59 mmol) and benzoquinone (129 mg, 1.18 mmol) in three portions over 1 hour. After 2 hours, the mixture was concentrated in vacuo and purified on $SiO_2$ (gradient elution, 0-70% EtOAc/hexanes) to yield the title compound. LRMS (ESI) m/z 786.5 [(M+H)$^+$; calculated for $C_{39}H_{53}ClN_5O_{10}$ 786.4].

Step 5: Ethyl (2R,6S,12Z,13aS,14aR,16aS)-6-amino-2-[(3-chloro-7-methoxyquinoxalin-2-yl)oxy]-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate

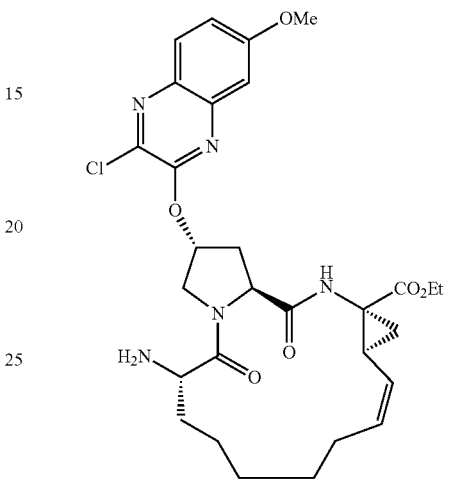

To a solution of the product from step 4 (31 g, 39.4 mmol) in toluene (310 mL) was added benzenesulfonic acid (12.47 g, 79 mmol). The mixture was then heated to 75° C. for 1 hour. The mixture was then cooled to RT and extracted with EtOAc/ 10% $NaHCO_3$. The organic layer was dried over $MgSO_4$, and concentrated in vacuo. The crude material was then used with no further purification in the next step. LRMS (ESI) m/z 586.4 [(M+H)$^+$; calculated for $C_{29}H_{37}ClN_5O_6$ 586.3].

Step 6: Ethyl (2R,6S,12Z,13aS,14aR,16aS)-2-[(3-chloro-7-methoxyquinoxalin-2-yl)oxy]-5,16-dioxo-6-[({[(1R,2R)-2-(pent-4-en-1-yl)cyclopentyl]oxy}carbonyl)amino]-1,2,3,6,7,8,9,10,11,13a,14,15,16,16a-tetradecahydrocyclopropa[e]pyrrolo[1,2-a][1,4]diazacyclopentadecine-14a(5H)-carboxylate

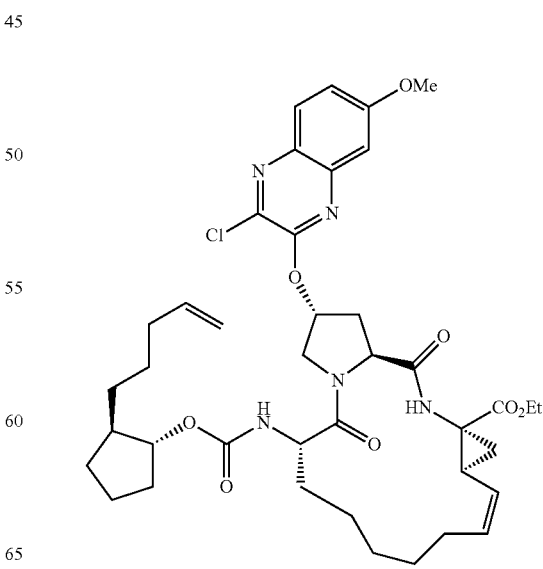

To a mixture of the product from step 5 (23.1 g, 39.4 mmol) in MeCN (250 mL) was added Et$_3$N (16.49 ml, 118 mmol) and Intermediate D1. (13.4 g, 45.3 mmol) in MeCN (60 mL). The reaction mixture was stirred at 40° C. for 30 minutes, and then extracted with EtOAc and 5% KHSO$_4$. The aqueous layer was re-extracted aqueous with EtOAc. The combined organic layers were washed with brine, dried over MgSO$_4$, and concentrated in vacuo. The crude material was purified on SiO$_2$ (gradient elution, 0-70% EtOAc/hexanes) to give the title compound. LRMS (ESI) m/z 766.6 [(M+H); calculated for C$_{40}$H$_{53}$ClN$_5$O$_8$ 766.4].

Step 7: Ethyl (2R,6S,12Z,13aS,14aR,16aS)-2-[(3-ethenyl-7-methoxyquinoxalin-2-yl)oxy]-5,16-dioxo-6-[({[(1R,2R)-2-(pent-4-en-1-yl)cyclopentyl]oxy}carbonyl)amino]-1,2,3,6,7,8,9,10,11,13a,14,15,16,16a-tetradecahydrocyclopropa[e]pyrrolo[1,2-a][1,4]diazacyclopentadecine-14a(5H)-carboxylate

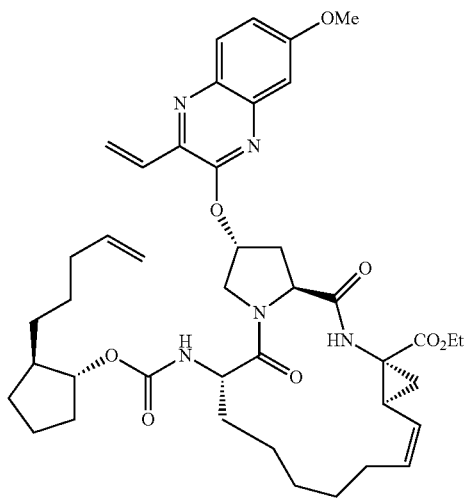 [SMILES: C=CCCC[C@@H]1CCC[C@H]1OC(=O)N[C@H]1CCCCC/C=C\[C@@H]2C[C@@]2(C(=O)OCC)NC(=O)[C@@H]2C[C@@H](Oc3nc4cc(OC)ccc4nc3C=C)CN2C1=O]

To a mixture of the product from step 6 (15 g, 19.57 mmol), CsF (6.5 g, 43.1 mmol), and BHT (0.216 g, 0.979 mmol) in dioxane (225 mL) under N$_2$ was added vinyltributyltin (8.6 ml, 29.4 mmol) and bis(tri-t-butylphosphine)palladium (0.5 g, 0.979 mmol). The mixture was heated to 70° C. under N$_2$ for 1 hour, diluted with EtOAc, and filtered through CELITE. The filtrate was then concentrated in vacuo and purified on SiO$_2$ (gradient elution, 0-70% EtOAc/hexanes) to yield the title compound. LRMS (ESI) m/z 758.6 [(M+H)$^+$; calculated for C$_{42}$H$_{56}$N$_5$O$_8$ 758.4].

Step 8: Ethyl (3aR,7S,13Z,14aS,15aR,18S,21R,29E,33aR)-25-methoxy-5,17,35-trioxo-1,2,3,3a,5,6,7,8,9,10,11,12,14a,15,17,18,20,21,31,32,33,33a-docosahydro-7,19:18,21-dimethanocyclopenta[28,29]cyclopropa[12,13][1,20,3,14,17]dioxatriazacyclononacosino[21,22-b]quinoxaline-15a(16H)-carboxylate

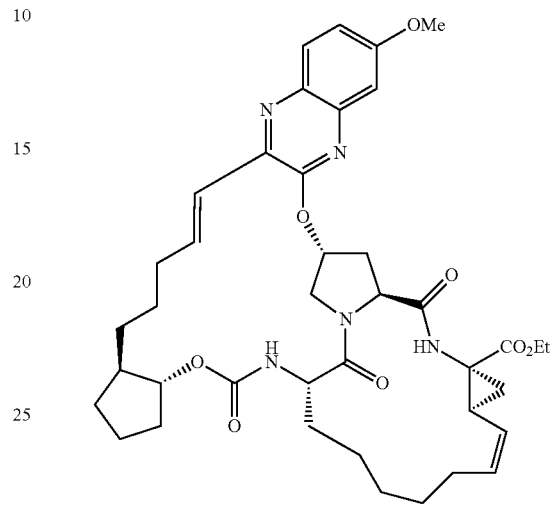

To a degassed solution of the product from step 7 (13.3 g, 17.55 mmol) in DCM (2.4 L) at reflux was added Zhan 1b catalyst (773 mg, 1.05 mmol) and benzoquinone (227 mg, 2.1 mmol) in three portions over 45 minutes. After 18 hours, the mixture was concentrated in vacuo and purified on SiO$_2$ (gradient elution, 0-75% EtOAc/hexanes) to yield the title compound. LRMS (ESI) m/z 730.6 [(M+H)$^+$; calculated for C$_{40}$H$_{52}$N$_5$O$_8$ 730.4].

Step 9: Ethyl (3aR,7S,13Z,14aS,15aR,18S,21R,33aR)-25-methoxy-5,17,35-trioxo-11,12,14a,15,17,18,20,21,29,30,31,32,33,33a-tetracosahydro-7,19:18,21-dimethanocyclopenta[28,29]cyclopropa[12,13][1,20,3,14,17]dioxatriazacyclononacosino[21,22-b]quinoxaline-15a(16H)-carboxylate

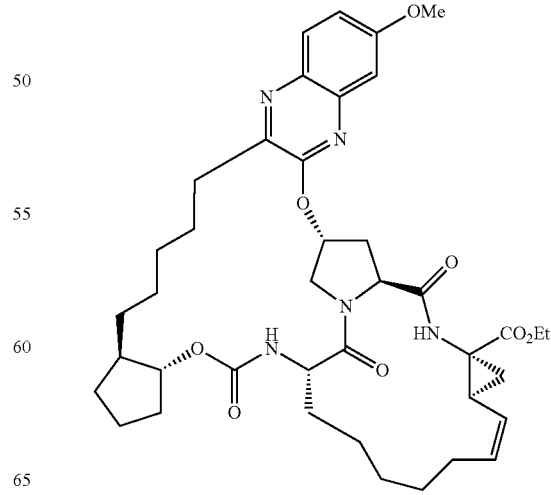

To a solution of the product from step 8 (16.8 g, 23.02 mmol) in EtOH (548 mL) was added bismuth(III)chloride (7.26 g, 23.02 mmol). The reaction was then cooled in an ice-salt bath to −17° C. internal temperature. KBH$_4$ (12.4 g, 230 mmol) was then added in aliquots keeping the internal temperature <−10° C. The resulting black suspension was then slowly warmed to 0° C. over 2 hours. The mixture was then diluted with EtOAc (500 mL), filtered through CELITE, and concentrated in vacuo. The residue was dissolved in EtOAc (300 mL), and H$_2$O (50 mL) was added. The pH was then adjusted with 0.5N HCl to pH<1. After separating the organic layer, the aqueous layer was washed with EtOAc. The combined organic layers were then extracted with NaHCO$_3$, washed with brine, dried over MgSO$_4$, and concentrated in vacuo. The crude material was then purified on SiO$_2$ (gradient elution, 0-60% EtOAc/hexanes) to yield the title compound. LRMS (ESI) m/z 732.6 [(M+11)$^+$; calculated for C$_{40}$H$_{54}$N$_5$O$_8$ 732.4].

Step 10: (3aR,7S,13Z,14aS,15aR,18S,21R,33aR)-25-methoxy-5,17,35-trioxo-1,2,3,3a,5,6,7,8,9,10,11,12,14a,15,17,18,20,21,29,30,31,32,33,33a-tetracosahydro-7,19:18,21-dimethanocyclopenta[28,29]cyclopropa[12,13][1,20,3,14,17]dioxatriazacyclononacosino[21,22-b]quinoxaline-15a(16H)-carboxylic acid

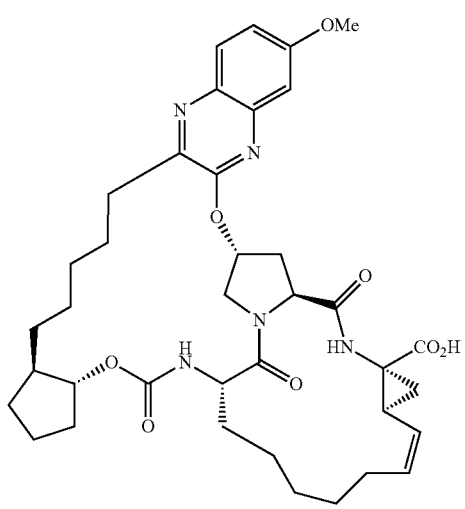 [SMILES: COc1ccc2nc3c(nc2c1)O[C@@H]1C[C@H]2C(=O)N[C@]4(C(=O)O)C[C@H]4/C=C\CCCCC[C@H](NC(=O)O[C@@H]4CCC[C@H]4CCCCC3)C(=O)N2C1]

To a solution of the product from step 9 (14.3 g, 19.54 mmol) in THF (200 mL), EtOH (50 mL), and H$_2$O (100 mL) was added LiOH (4.68 g, 195 mmol). The mixture was heated to 40° C. for 4 hours, cooled to RT, and pH adjusted to 2 with 1N HCl. The resulting solid was collected by filtration, washed with H$_2$O, and combined with the material isolated from the extraction of the aqueous layer. The aqueous layer was then extracted with EtOAc two times. The combined organic layers were washed with brine, dried over MgSO$_4$, and concentrated in vacuo. The combined residues were then taken up in DCM and precipitated with Et$_2$O to give, after filtration, the title compound as a solid. LRMS (ESI) m/z 704.6 [(M+H)$^+$; calculated for C$_{38}$H$_{50}$N$_5$O$_8$ 704.4].

Step 11: (3R,20R,24R,28S,34Z,36S,38R,41S)—N-(Cyclopropylsulfonyl)-9-methoxy-26,40,42-trioxo-4,25-dioxa-1,6,13,27,39-pentaazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide To a mixture of the product from step 10 (460 mg, 0.654 mmol) in THF (22 mL) was added CDI (318 mg, 1.96 mol), and the resulting mixture was heated to 50° C. for 2 hours. Intermediate B1 (475 mg, 3.92 mmol) and DBU (0.59 mL, 3.92 mmol) were then added, and stirring was continued for 1 hours. The reaction was then cooled to RT and extracted with EtOAc and 0.5M HCl. The organic layer was washed with brine, dried over Na$_2$SO$_4$, and concentrated in vacuo. The crude material was then purified on SiO$_2$ (gradient elution, 0-25% acetone/DCM), and then titrated with DCM. The mother liquors were then concentrated in vacuo to yield the title compound. LRMS (ESI) m/z 807.8 [(M+H)$^+$; calculated for C$_{41}$H$_{55}$N$_6$O$_9$S 807.4].

Example 2

(3R,20R,24R,28S,34Z,36S,38R,41S)-9-Methoxy-N-[(1-methylcyclopropyl)sulfonyl]-26,40,42-trioxo-4,25-dioxa-1,6,13,27,39-pentaazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide

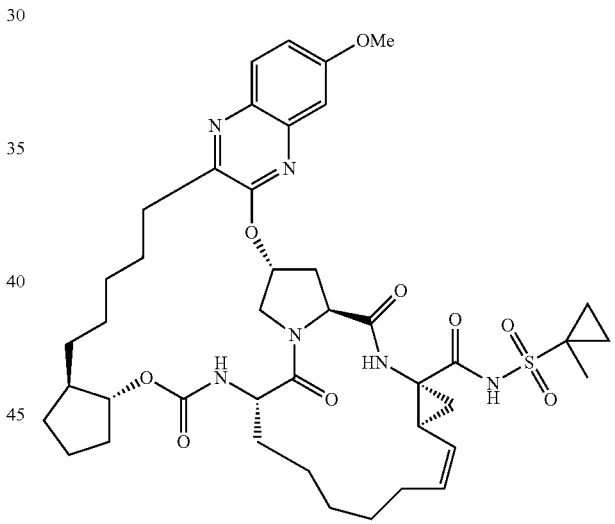

To a mixture of the product from Example 1, step 10 (5.4 g, 7.67 mmol) in THF (96 mL) was added CDI (1.74 g, 10.74 mmol), and the resulting mixture was heated to 40° C. for 30 minutes. Intermediate B2 (1.56 g, 11.51 mmol) and DBU (2.3 mL, 15.34 mmol) were then added, and stirring was continued for 20 hours. The reaction was then cooled to RT and extracted with EtOAc and 5% KHSO$_4$. The organic layer was washed with NaHCO$_3$ and brine, dried over MgSO$_4$, and concentrated in vacuo. The crude material was then purified on SiO$_2$ (gradient elution, 0-30% acetone/DCM). The resulting material was then dissolved in 30% EtOAc/hexanes at 35 mL/g and stirred 18 hours. The resulting solid was collected and dried in vacuo to yield the title compound LRMS (ESI) m/z 821.6 [(M+H)$^+$; calculated for C$_{42}$H$_{57}$N$_6$O$_9$S 821.4].

Example 3

(3R,20R,22R,26S,32Z,34S,36R,39S)—N-(Cyclopropylsulfonyl)-9-methoxy-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

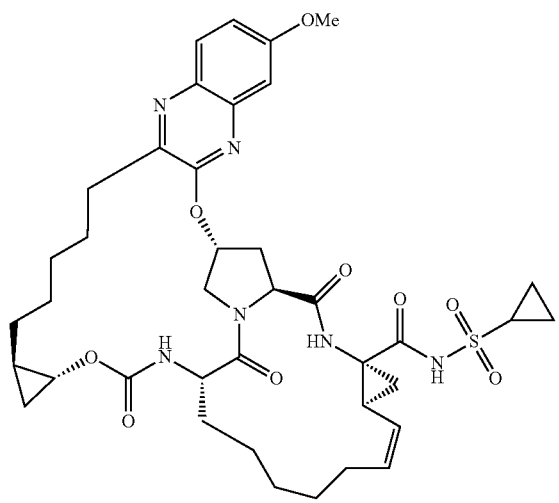 [SMILES: COc1ccc2nc3c(nc2c1)O[C@@H]1C[C@H]2C(=O)N[C@]4(C(=O)NS(=O)(=O)C5CC5)C[C@H]4/C=C\CCCCC[C@H](NC(=O)O[C@@H]4C[C@H]4CCCCC3)C(=O)N2C1]

The title compound can be prepared according to the procedures in Example 1 using Intermediate D2 in step 6. LRMS (ESI) m/z 779.4 [(M+11)$^+$; calculated for C$_{39}$H$_{51}$N$_6$O$_9$S 779.4].

Example 4

(3R,20R,22R,26S,32Z,34S,36R,39S)-9-Methoxy-N-[(1-methylcyclopropyl)sulfonyl]-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

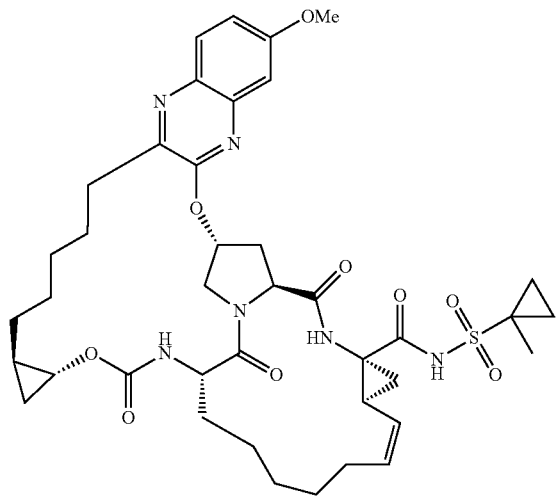 [SMILES: COc1ccc2nc3c(nc2c1)O[C@@H]1C[C@H]2C(=O)N[C@]4(C(=O)NS(=O)(=O)C5(C)CC5)C[C@H]4/C=C\CCCCC[C@H](NC(=O)O[C@@H]4C[C@H]4CCCCC3)C(=O)N2C1]

The title compound can be prepared according to the procedures in Example 1 using Intermediates D2 and B2 in steps 6 and 11, respectively. LRMS (ESI) m/z 793.6 [(M+H)$^+$; calculated for C$_{40}$H$_{53}$N$_6$O$_9$S 793.4].

Example 5

(3R,20R,22R,26S,32Z,34S,36R,39S)—N-(Cyclopropylsulfonyl)-9-methoxy-22-methyl-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

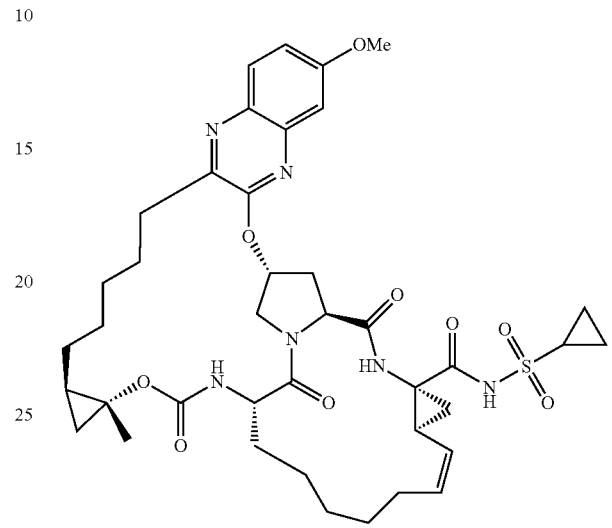

The title compound can be prepared according to the procedures in Example 1 using Intermediate D3 in step 6. LRMS (ESI) m/z 793.6 [(M+H)$^+$; calculated for C$_{40}$H$_{53}$N$_6$O$_9$S 793.4].

Example 6

(3R,20R,22R,26S,32Z,34S,36R,39S)-9-Methoxyl-22-methyl-N-[(1-methylcyclopropyl)sulfonyl]-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

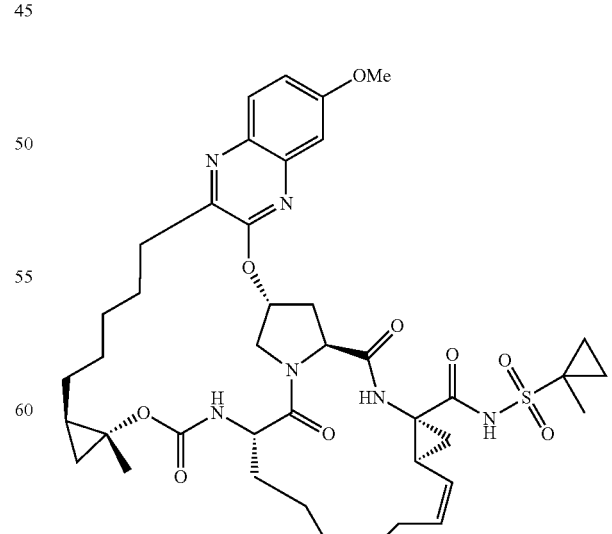

The title compound can be prepared according to the procedures in Example 1 using Intermediates D3 and B2 in steps 6 and 11, respectively. LRMS (ESI) m/z 807.6 [(M+H)$^+$; calculated for $C_{41}H_{55}N_6O_9S$ 807.4].

Example 7

(3R,20R,24R,28S,34Z,36S,38R,41S)—N-[(1-Methylcyclopropyl)sulfonyl]-26,40,42-trioxo-4,25-dioxa-1,6,13,27,39-pentaazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide

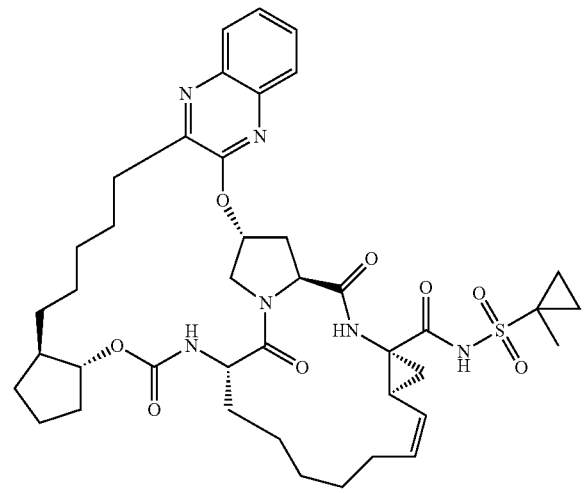 [SMILES: CC1(S(=O)(=O)NC(=O)[C@@]23C[C@H]2/C=C\CCCCC[C@@H]2NC(=O)O[C@@H]4CCC[C@H]4CCCCCc4nc5ccccc5nc4O[C@@H]4C[C@@H](C(=O)N3)N(C4)C2=O)CC1]

The title compound can be prepared according to the procedures in Example 1 using Intermediates E2 and 132 in steps 1 and 11, respectively. LRMS (ESI) m/z 791.5 [(M+H)$^+$; calculated for $C_{41}H_{55}N_6O_8S$ 791.4].

Example 8

(3R,20R,22R,26S,32Z,34S,36R,39S)—N-(Cyclopropylsulfonyl)-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

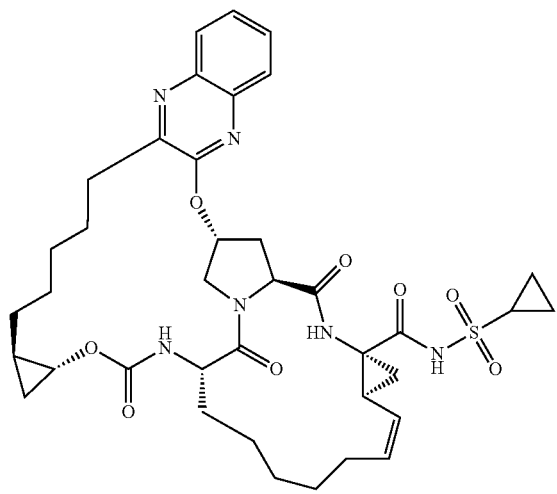 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)Oc2nc3ccccc3nc2CCCCC[C@@H]2C[C@H]2O1]

The title compound can be prepared according to the procedures in Example 1 using Intermediates E2 and D2 in steps 1 and 6, respectively. LRMS (ESI) m/z 749.5 [(M+H)$^+$; calculated for $C_{38}H_{49}N_6O_8S$ 749.4].

Example 9

(3R,20R,22R,26S,32Z,34S,36R,39S)—N-[(1-Methylcyclopropyl)sulfonyl]-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

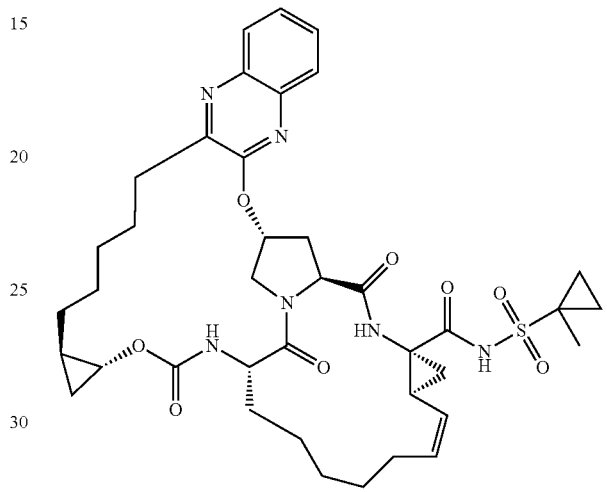

The title compound can be prepared according to the procedures in Example 1 using Intermediates E2, D2, and B2 in steps 1, 6 and 11, respectively. LRMS (ESI) m/z 763.5 [(M+H)$^+$; calculated for $C_{39}H_{51}N_6O_8S$ 763.4].

Example 10

(3R,20R,22R,26S,32Z,34S,36R,39S)—N-(Cyclopropylsulfonyl)-22-methyl-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

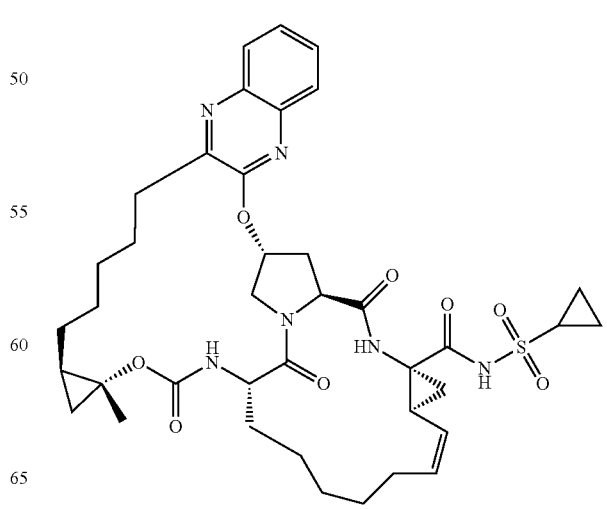

The title compound can be prepared according to the procedures in Example 1 using Intermediates E2 and D3 in steps 1 and 6, respectively. LRMS (ESI) m/z 763.5 [(M+H)+; calculated for $C_{39}H_{51}N_6O_8S$ 763.4].

Example 11

(3R,20R,22R,26S,32Z,34S,36R,39S)-22-Methyl-N-[(1-methylcyclopropyl)sulfonyl]-24,38,40-trioxo-4,23-dioxa-1,6,13,25,37-pentaazaheptacyclo[24.13.1.1$^{3,39}$.0$^{5,14}$.0$^{7,12}$.0$^{20,22}$.0$^{34,36}$]hentetraconta-5,7,9,11,13,32-hexaene-36-carboxamide

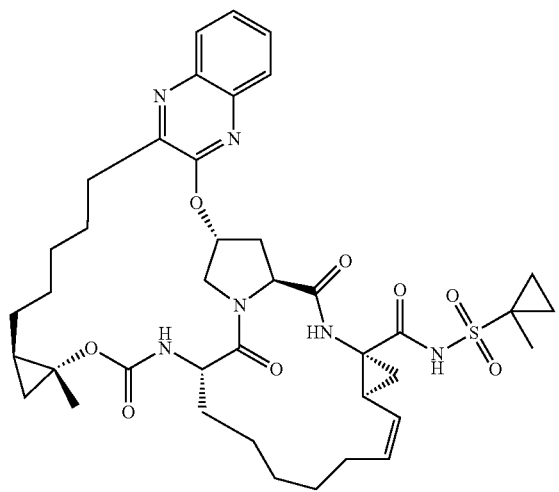 [SMILES: CC1(S(=O)(=O)NC(=O)[C@@]23C[C@H]2/C=C\CCCCC[C@@H]2NC(=O)O[C@]4(C)C[C@H]4CCCCCc4nc5ccccc5nc4O[C@@H]4C[C@@H](C(=O)N3)N(C4)C2=O)CC1]

The title compound can be prepared according to the procedures in Example 1 using Intermediates E2, D3, and B2 in steps 1, 6 and 11, respectively. LRMS (ESI) m/z 777.5 [(M+H)+; calculated for $C_{40}H_{53}N_6O_8S$ 777.4].

Example 12

Comparison of Different Compounds

The compounds of Examples 1 through 11 were compared to the compound of Example 18 of WO 2008/057208. The results are shown in Tables 1 and 2 below. As illustrated in the tables and the discussion of the results, compounds of Formula I, as illustrated by the compounds of Examples 1 through 11, appear to have several advantageous properties compared to the compound of Example 18 of WO 2008/057208.

The activity tables provided below illustrates the observed activity:

TABLE 1

| NS3/4A Inhibitory Activity (Ki) | | | |
|---|---|---|---|
| | Enzyme Activity (nM) | | |
| Compound | gt 1b $K_i$ | gt 1b A156V $K_i$ | gt 3a $K_i$ |
| WO 2008/057208 Example 18 | 0.85 | 8.7 | 1.88 |
| Example 1 | 0.16 | 1.6 | 0.45 |
| Example 2 | 0.05 | 1.1 | 0.48 |
| Example 3 | 0.02 | 0.8 | 0.24 |
| Example 4 | 0.04 | 0.6 | 0.27 |

TABLE 1-continued

| NS3/4A Inhibitory Activity (Ki) | | | |
|---|---|---|---|
| | Enzyme Activity (nM) | | |
| Compound | gt 1b $K_i$ | gt 1b A156V $K_i$ | gt 3a $K_i$ |
| Example 5 | 0.02 | 0.7 | 0.25 |
| Example 6 | 0.03 | 0.6 | 0.32 |
| Example 7 | 0.02 | 1.2 | 0.72 |
| Example 8 | 0.02 | 0.9 | 0.49 |
| Example 9 | 0.03 | 0.8 | 0.52 |
| Example 10 | 0.02 | 0.6 | 0.35 |
| Example 11 | 0.02 | 0.5 | 0.37 |

$K_i$: Inhibition constant; gt: Genotype.

TABLE 2

| Compound Inhibitory Potency (Replicon (nM)) and In-Vivo Covalent Binding | | | | |
|---|---|---|---|---|
| | gt 1b Replicon | | Rat PK | |
| | $EC_{50}$ (nM) | | 5 mpk [liver] | 5 mpk |
| Compound | 10% FBS | 50% NHS | 4 h (nM) | AUC (nMh) |
| WO 2008/057208 Example 18 | 4 | 22 | Not Available | Not Available |
| Example 1 | 2 | 9 | 3600 | 0 |
| Example 2 | 2 | 10 | 43000 | 0.55 |
| Example 3 | 2 | 8 | 13000 | 0.19 |
| Example 4 | 2 | 4 | 19000 | 0.1 |
| Example 5 | 1 | 6 | 20000 | 0.18 |
| Example 6 | 1 | 4 | 24000 | 0.16 |
| Example 7 | 2 | 10 | 41000 | 1.35 |
| Example 8 | 1 | 13 | 7000 | 0.06 |
| Example 9 | 2 | 11 | 20000 | 0.26 |
| Example 10 | 1 | 5 | 15000 | 0.6 |
| Example 11 | 1 | 5 | 4000 | 0.07 |

$EC_{50}$: Effective concentration achieving 50% viral replication suppression; FBS: fetal bovine serum; NHS: normal human serum; AUC: Area under the plasma concentration/time curve.

Methods

Compounds described herein were analyzed for different activities such as the ability to inhibit HCV NS3 activity, HCV replicon activity, and HCV replication activity using techniques well-known in the art. See, for example, Steven S. Carroll et al., *Inhibition of Hepatitis C Virus RNA Replication by 2'-Modified Nucleoside Analogs*, 278(14) J. BIOLOGICAL CHEMISTRY 11979 (2003).

Measuring NS3/4A Inhibitory Activity ($K_i$)

Compounds were analyzed using the HCV NS3 protease time-resolved fluorescence (TRF) assay as described below and in Shi-Shan Mao et al., *A time-resolved, internally quenched fluorescence assay to characterize inhibition of hepatitis C virus nonstructural protein 3-4A protease at low enzyme concentrations*, 373 ANALYTICAL BIOCHEMISTRY 1 (2008), and WO 2006/102087. This NS3 protease assay was performed in a final volume of 100 µl assay buffer containing 50 mM HEPES, pH 7.5, 150 mM NaCl, 15% glycerol, 0.15% TRITON X-100, 10 mM DTT, and 0.1% PEG 8000. NS3/4A protease was pre-incubated with various concentrations of inhibitors in DMSO for 30 minutes. The reaction was initiated by adding the TRF peptide substrate (final concentration 100 nM). NS3 mediated hydrolysis of the substrate was quenched after 1 hour at RT with 100 µl of 500 mM MES, pH 5.5. Product fluorescence was detected using either a VICTOR V2 or FUSION fluorophotometer (PERKIN ELMER LIFE AND ANALYTICAL SCIENCES) with excitation at 340 nm and emission at 615 nm with a 400 us delay. Testing concentrations of different enzyme forms were selected to result in a signal to background ratio (SIB) of 10-30. $IC_{50}$ values were derived using a standard four-parameter fit to the data. $K_i$ values are derived from $IC_{50}$ values using the following formula, $$IC_{50}=K_i(1+[S]/K_M),\qquad\text{Eqn (1),}$$

where [S] is the concentration of substrate peptide in the reaction and $K_M$ is the Michaelis constant. See Paola Gallinari et al., *Modulation of Hepatitis C Virus NS3 Protease and Helicase Activities through the Interaction with NS4A*, 38 BIOCHEM. 5620 (1999); Paola Gallinari et al., *Multiple Enzymatic Activities Associated with Recombinant NS3 Protein of Hepatitis C Virus*, 72(8) J. VIROLOGY 6758 (1998); Mariana Milani et al., *A Continuous Assay of Hepatitis C Virus Protease Based on Resonance Energy Transfer Depsipeptide Substrates*, 240 ANAL. BIOCHEM. 60 (1996); Shi-Shan Mao et al., *A time-resolved, internally quenched fluorescence assay to characterize inhibition of hepatitis C virus nonstructural protein 3-4A protease at low enzyme concentrations*, 373 ANALYTICAL BIOCHEMISTRY 1 (2008).

Measuring Compound Inhibitory Potency (Replicon $EC_{50}$ (nM))

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicon-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

Stable neomycin phosphotransferase encoding replicon-harboring cell lines were used, so all cell lines were maintained under G418 selection prior to the assay. In some cases the cell lines encoded a luciferase:NEO FUSION and could be assayed either directly by determination of RNA copy number, or indirectly through measurement of the luciferase activity.

To initiate an assay, replicon cells were plated in the presence of a dilution series of test compound in the absence of G418. Typically, the assays were performed in a 96-well plate format for manual operation, or a 384-well plate in an automated assay. Replicon cells and compound were incubated for 24 to 48 hours, depending on the assay. At the end of the assay, cells are washed free of media and compound and then lysed. For direct quantitation, RNA levels were measured by 32P-probe hybridization and protection, or in a TAQMAN-based assay and normalized to cellular cyclophilin A RNA levels. In some cases, luciferase activity was measured using a conventional luciferase assay. In all cases, $EC_{50}$ determinations were calculated as a percent of a DMSO control by fitting the data to a four-parameter fit function.

Plasma and Liver Concentrations and Pharmacokinetics

Test compounds were dissolved in a suitable dosing vehicle for i.v. administration (e.g., 20%:60%:20% DMSO: PEG400:H$_2$O) or per oral administration (e.g., 10% POLYSORBATE80:90% H$_2$O or 100% PEG400). Animals were administered (n=2 or 3) using a crossover study design for non-rodents. Plasma samples were collected at time points between 2 minutes and 24 hours, and compound levels were determined by RP-LC/MS/MS. Liver samples were collected post-mortem in rat. Liver samples were weighed, homogenized, and diluted using techniques known to those skilled in the art, and compound levels were determined by RP-LC/MS/MS.

Pharmacokinetic parameters were calculated based on non-compartmental analysis (e.g., using WATSON, WINNOLIN). Predose concentrations that were below the limit of quantitation (BLQ) were assigned a value of 0, Standard pharmacokinetic parameters CLp, Vdss, half-life (only for IV), % F, $C_{max}$, $T_{max}$, $AUC_{0\text{-}last}$, $AUC_{0\text{-}infinity}$ were calculated. AUC values were calculated using linear trapezoidal method for ascending concentrations and the log trapezoidal method for descending concentrations.

It will be appreciated that various of the above-discussed and other features and functions, or alternatives thereof, may be desirably combined into many other different systems or applications. Also various presently unforeseen or unanticipated alternatives, modifications, variations or improvements on the above-described and herein claimed subject matter may be subsequently made by those skilled in the art and are also intended to be encompassed by the following claims.

What is claimed is:

1. A compound, or a pharmaceutically acceptable salt, solvate or hydrate thereof, selected from the group consisting of:

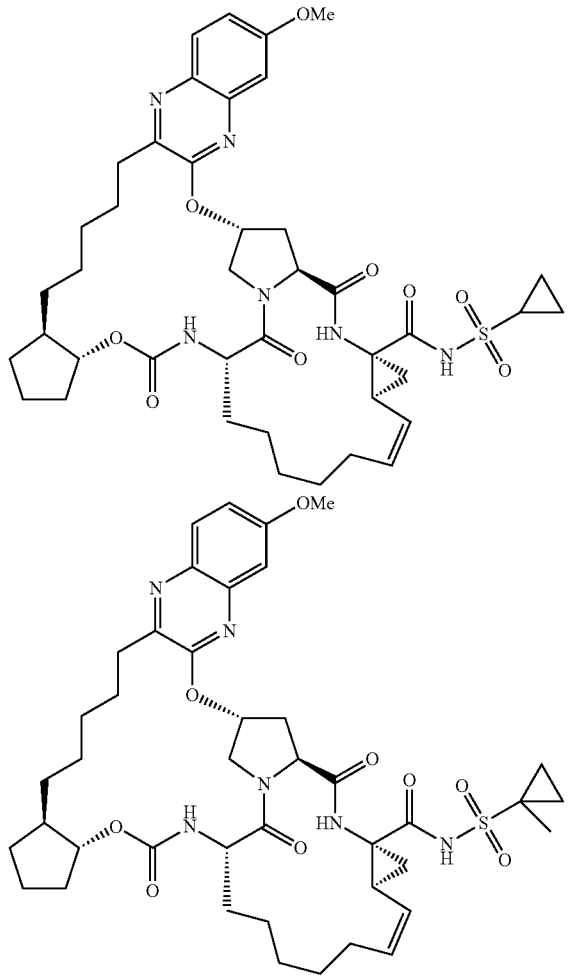

61
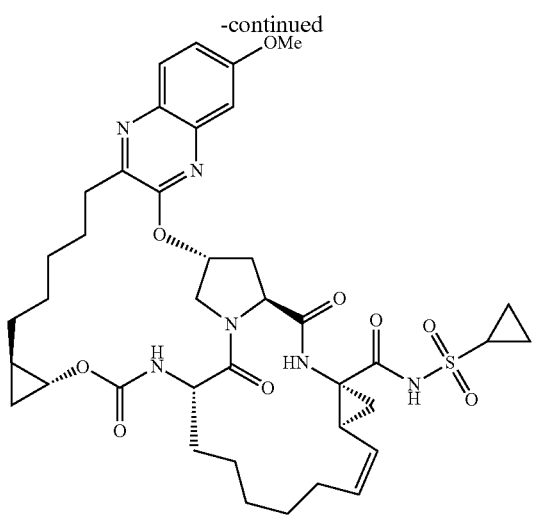
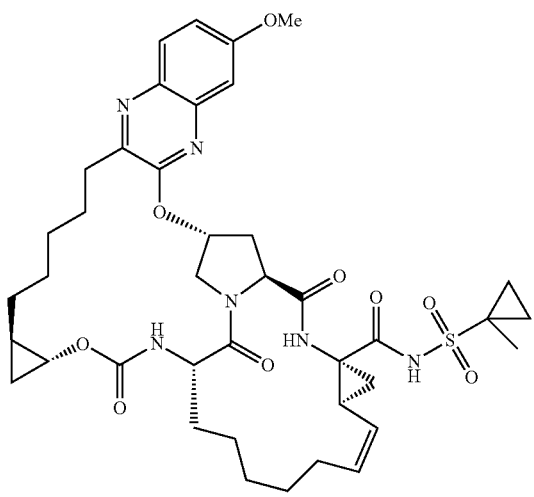
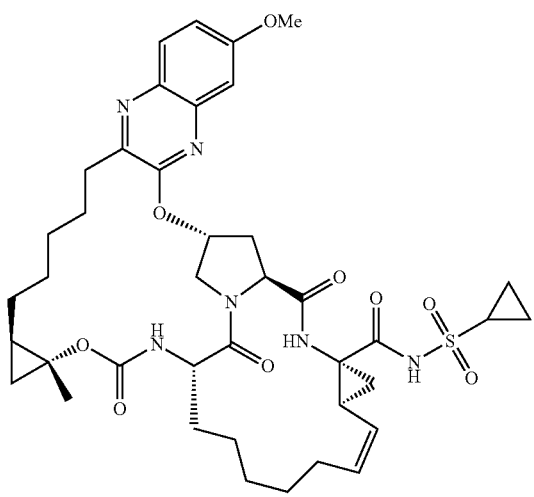
62
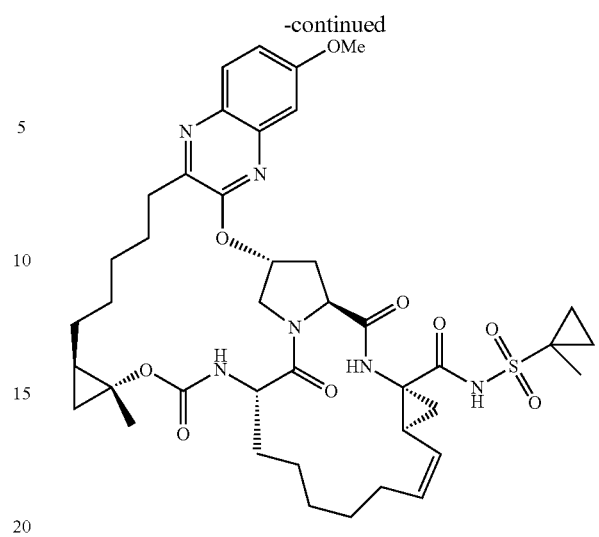
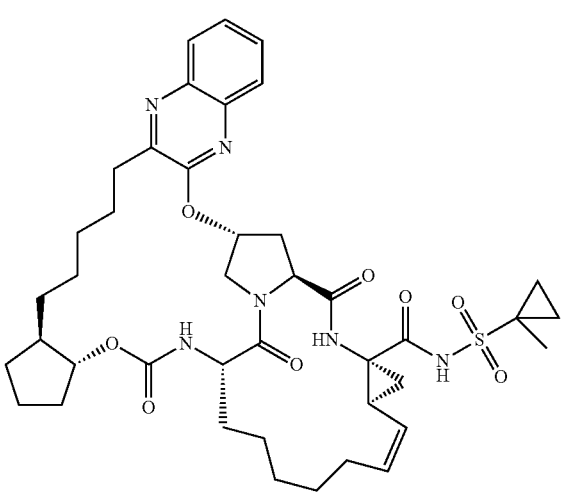
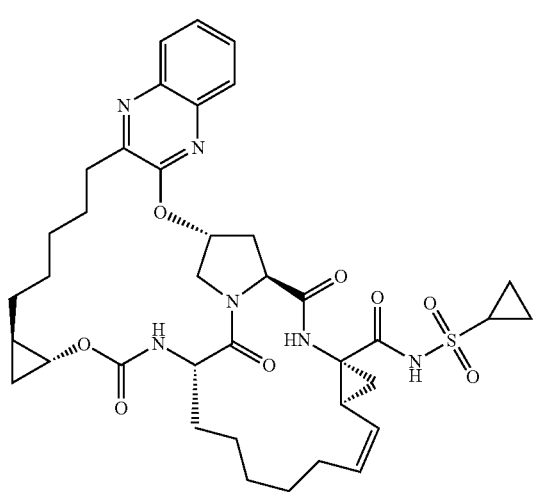

2. The compound according to claim 1, or a pharmaceutically acceptable salt, solvate or hydrate thereof, selected from the group consisting of:

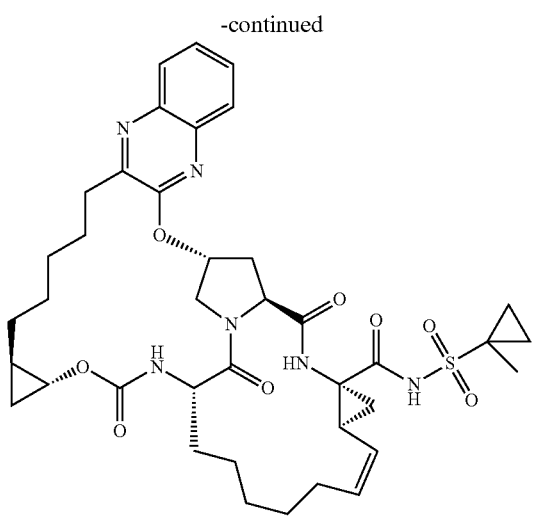

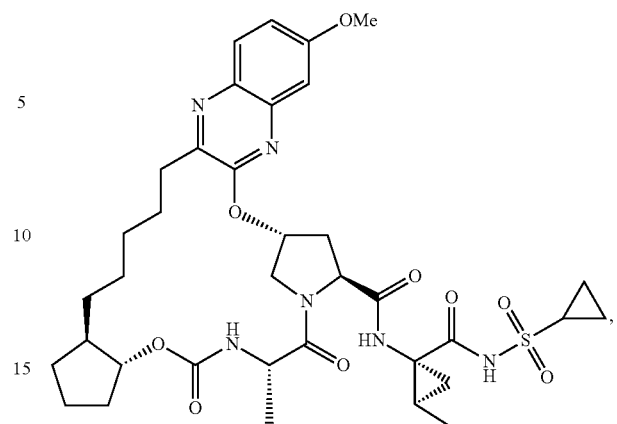

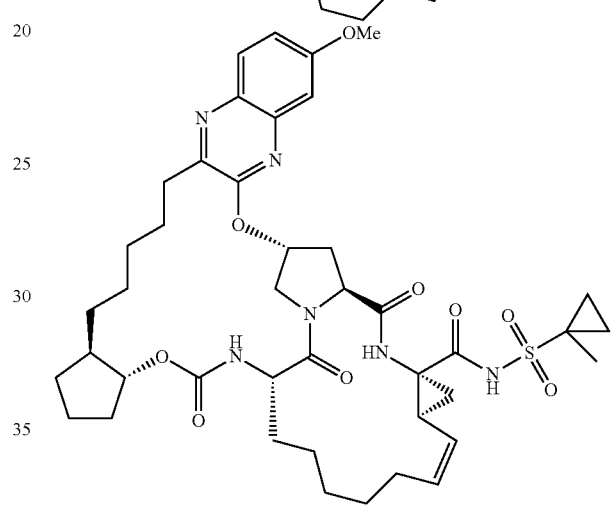

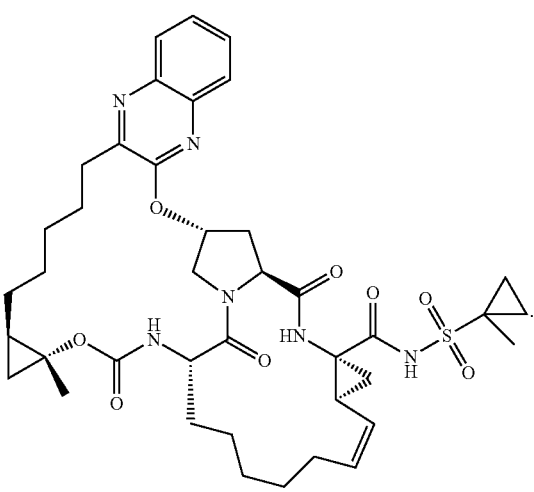

and

3. A pharmaceutical composition comprising an effective amount of a compound according claim 1, and a pharmaceutically acceptable carrier.

4. The pharmaceutical composition according to claim 3, further comprising at least one additional therapeutic agent independently selected from the group consisting of a HCV antiviral agent, an immunomodulator, and an anti-infective agent.

5. The pharmaceutical composition according to claim 4, wherein the HCV antiviral agent is an antiviral selected from the group consisting of a HCV protease inhibitor and a HCV NS5B polymerase inhibitor.

6. A method of treating infection by HCV in a subject in need thereof, said method comprising administering to the subject an effective amount of a compound according to claim 1.

\* \* \* \* \*